(12) United States Patent
Misharin

(10) Patent No.: US 10,925,496 B2
(45) Date of Patent: Feb. 23, 2021

(54) METHODS AND SYSTEMS FOR OBTAINING PHYSIOLOGIC INFORMATION

(71) Applicant: Alexander Misharin, North Wales, PA (US)

(72) Inventor: Alexander Misharin, North Wales, PA (US)

( * ) Notice: Subject to any disclaimer, the term of this patent is extended or adjusted under 35 U.S.C. 154(b) by 604 days.

(21) Appl. No.: 15/650,850

(22) Filed: Jul. 15, 2017

(65) Prior Publication Data

US 2018/0014736 A1 Jan. 18, 2018

Related U.S. Application Data

(60) Provisional application No. 62/363,230, filed on Jul. 16, 2016.

(51) Int. Cl.
| | | |
|---|---|---|
| *A61B 5/024* | (2006.01) | |
| *A61B 5/00* | (2006.01) | |
| *G06T 7/00* | (2017.01) | |
| *A61B 5/08* | (2006.01) | |
| *G06T 7/246* | (2017.01) | |

(52) U.S. Cl.
CPC ........ *A61B 5/02405* (2013.01); *A61B 5/0077* (2013.01); *A61B 5/0082* (2013.01); *A61B 5/024* (2013.01); *A61B 5/0816* (2013.01); *G06T 7/0012* (2013.01); *G06T 7/246* (2017.01); *A61B 2562/04* (2013.01); *G06T 2207/10016* (2013.01); *G06T 2207/10048* (2013.01); *G06T 2207/20056* (2013.01); *G06T 2207/30048* (2013.01); *G06T 2207/30196* (2013.01)

(58) Field of Classification Search
CPC ............. A61B 5/02405; A61B 5/0077; A61B 5/0082; G06T 7/0012; G06T 2207/30048
USPC .......................................................... 348/77
See application file for complete search history.

(56) References Cited

U.S. PATENT DOCUMENTS

| | | | |
|---|---|---|---|
| 5,249,163 | A | 9/1993 | Erickson |
| 6,352,517 | B1 | 3/2002 | Flock |
| 7,477,571 | B2 | 1/2009 | Melese |
| 8,693,735 | B2 | 4/2014 | Kielkopf |
| 8,792,969 | B2 | 7/2014 | Bernal |
| 8,855,384 | B2 | 10/2014 | Kyal |

(Continued)

OTHER PUBLICATIONS

Chen J., Chang Z., Qiu Q., Li X., Sapiro G., Bronstein A., Pietikäinen M. "RealSense=Real Heart Rate: Illumination Invariant Heart Rate Estimation from Videos", 6th International Conference on Image Processing Theory Tools and Applications (IPTA), Dec. 12-15, 2016, Oulu, Finland, DOI: doi.org/10.1109/IPTA.2016.7820970; 6 pages.

(Continued)

*Primary Examiner* — On S Mung

(57) ABSTRACT

The present invention discloses methods suitable for obtaining information related to at least one physiologic parameter of a person belonging to the group comprising respiration rate, heart rate, respiration rate variability, heart rate variability, temporal characteristics of at least a part of a heartbeat, and temporal characteristics of at least a part of a respiration cycle in a non-contact fashion. The present invention also discloses systems suitable for obtaining information related to at least one physiologic parameter of a person belonging to said group of physiologic parameters in a non-contact fashion.

27 Claims, 14 Drawing Sheets

(56) References Cited

U.S. PATENT DOCUMENTS

| | | | |
|---|---|---|---|
| 8,897,522 | B2 | 11/2014 | Mestha |
| 8,971,985 | B2 | 3/2015 | Bernal |
| 9,204,824 | B2 | 12/2015 | Lasenby |
| 9,204,825 | B2 | 12/2015 | Lasenby |
| 9,226,691 | B2 | 1/2016 | Bernal |
| 9,262,826 | B2 | 2/2016 | Khachaturian |
| 9,265,456 | B2 | 2/2016 | Kirenko |
| 9,301,710 | B2 | 4/2016 | Mestha |
| 9,305,350 | B2 | 4/2016 | Crawley |
| 9,324,144 | B2 | 4/2016 | Khachaturian |
| 9,364,157 | B2 | 6/2016 | Lu |
| 9,636,041 | B2 | 5/2017 | Zalevsky |
| 2011/0142316 | A1* | 6/2011 | Wang .................. G06T 11/006 382/131 |
| 2013/0324875 | A1* | 12/2013 | Mestha ................ A61B 5/1077 600/534 |
| 2014/0072190 | A1 | 3/2014 | Wu |

OTHER PUBLICATIONS

Nakajima K., Osa A., Miike H. "A method for measuring respiration and physical activity in bed by optical flow analysis" in Proceedings of the 19th Annual International Conference of the IEEE Engineering in Medicine and Biology Society, Oct. 30-Nov. 2, 1997, Chicago, IL, USA, vol. 5, pp. 2054-2057, DOI: doi.org/10.1109/IEMBS.1997.758752.

Nakajima K., Matsumoto Y., Tamura T. "Development of real-time image sequence analysis for evaluating posture change and respiratory rate of a subject in bed", Physiological Measurement, 2001, vol. 22, No. 3, pp. N21-N28, DOI: doi.org/10.1088/0967-3334/22/3/401.

Kuo Y.-M., Lee J.-S., Chung P.-C. "A Visual Context-Awareness-Based Sleeping-Respiration Measurement System", IEEE Transactions on Information Technology in Biomedicine, 2010, vol. 14, issue 2, pp. 255-265, DOI: doi.org/10.1109/TITB.2009.2036168.

* cited by examiner

METHODS AND SYSTEMS FOR OBTAINING PHYSIOLOGIC INFORMATION

CROSS-REFERENCE TO RELATED APPLICATIONS

This application claims priority from U.S. Provisional Patent Application No. 62/363,230 filed Jul. 16, 2016, which is incorporated herein by reference.

BACKGROUND OF THE INVENTION

The ability to register pulse, respiration and other mechanical movements of a person in a non-contact fashion with high temporal resolution (at e.g. about 100 measurements per second) over extended periods of time (e.g. many hours) can find important applications in the fields of sleep medicine, cardiology, and in situations when direct contact with a person for the purpose of obtaining such measurements is either undesirable or not possible.

The present invention discloses methods suitable for obtaining information related to at least one physiologic parameter of a person belonging to the group comprising respiration rate, heart rate, respiration rate variability, heart rate variability, temporal characteristics of at least a part of a heartbeat, and temporal characteristics of at least a part of a respiration cycle (referred to as "physiologic parameters" below) in a non-contact fashion. The present invention also discloses systems suitable for obtaining information related to at least one physiologic parameter of a person belonging to said group of physiologic parameters in a non-contact fashion.

The methods and systems of the present invention can find applications in the areas of respiration and/or pulse gating for medical imaging (magnetic resonance imaging (MRI), X-ray computed tomography, etc.), sleep studies for non-contact monitoring of said physiologic parameters during a person's sleep (see FIGS. 4A-B, 5A-B, and 6, and the related discussion below), and in other areas. The methods and systems according to the present invention can be used as non-contact analogs of seismocardiography and ballistocardiography methods and devices used for monitoring mechanical activity of a heart (see FIGS. 7 and 8A-B, and the related discussion below).

DETAILED DESCRIPTION OF THE INVENTION

Three key elements of the present invention are: a light source element which main function is to illuminate a set of areas of a person's body, said set of areas may be at least partially covered by a cloth or an item of clothing or a blanket or any other covering item or items (we assume that a person's body or a part of a person's body or any number of areas of a person's body can be either covered completely or covered partially or not covered at all when we make references to a "person's body" or a "part of a person's body" or an "area of a person's body" or a "set of areas of a person's body" or "two areas of the person's body" or to any number of the areas of a person's body below, including the Claims of the present invention); a video camera element which main function is to collect a set of video frames for at least a part of said illuminated areas; and a computing element which main function is to perform computations for at least a part of said video frames set. Said elements and their function are described in greater details below.

Video frame is defined as a set of numeric values corresponding to a set of pixels of a video sensor of the video camera element; the set of pixels can be however large or small, ranging from all the sensor pixels (the whole sensor) to two of the sensor's pixels; said set of numeric values can contain more than one numeric value corresponding to the same pixel of the video sensor. Pixel of a video frame is defined as a set of numeric values corresponding to a single pixel of a video sensor of the video camera element.

The main effect of a light source element and of its function according to the present invention is to impart an additional (to the present or non-present ambient (natural or artificial) light) light texture to a part of a person's body. We term the additional light texture the "artificial light texture" or the "ALT". The additional light texture is preferably characterized by having a number of distinct illumination areas which we term its "elements". For example, a set of light spots created by a light source element on different areas of a person's body forms said artificial light texture with each individual light spot being its element.

Figure 9:
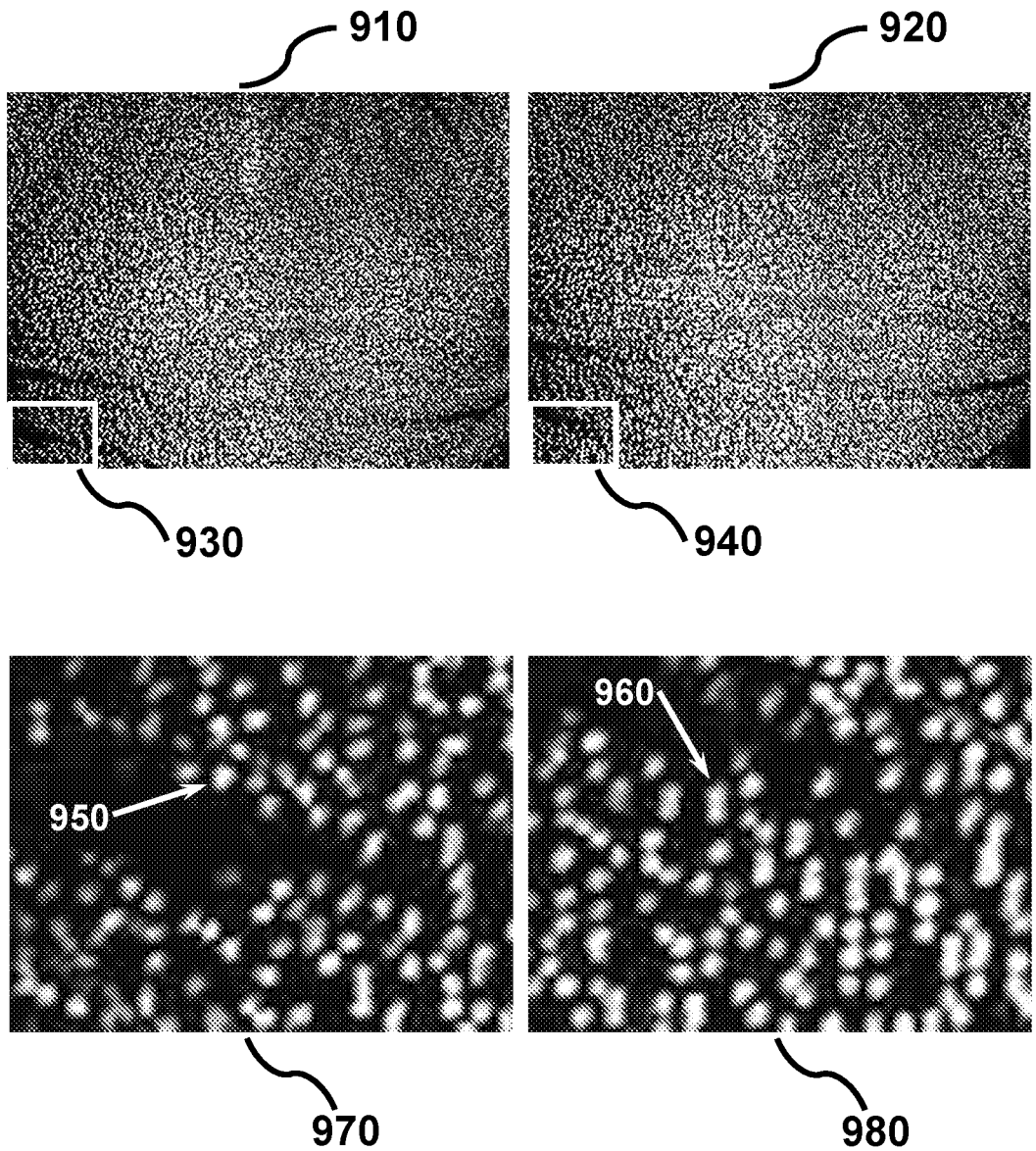
FIG. 9 shows variation of the elements of the additional light texture associated with the respiration and/or pulse of a person.
Figure 10:
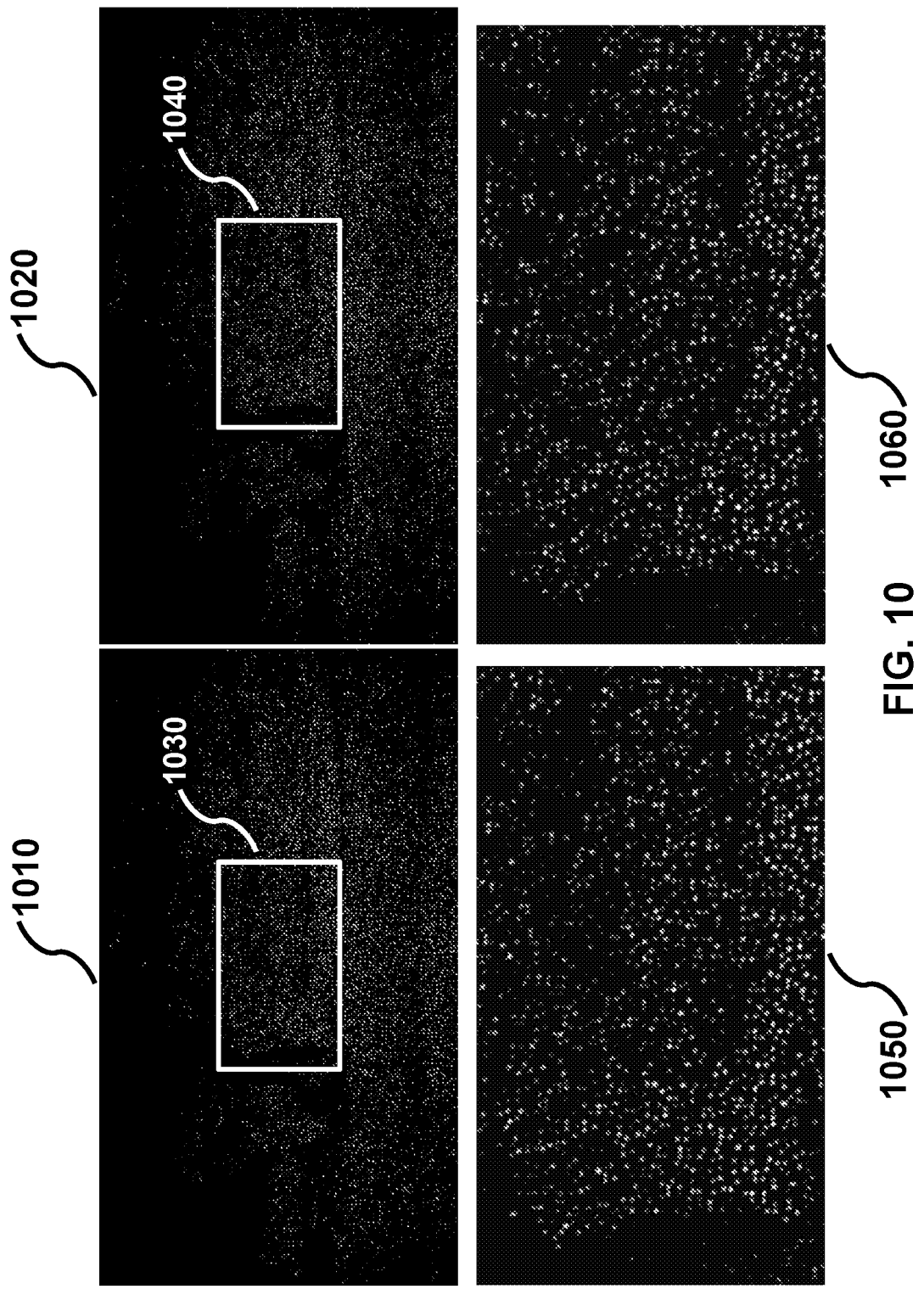
FIG. 10 shows variation of the elements of the additional light texture associated with the respiration and/or pulse of a person.

Movements of a person's body, including those which are related to the person's respiration and/or heartbeat, can lead to a change in the curvature and/or position and/or tilt and/or size of the surfaces of the person's body parts and/or of any of said items which might be covering the person's body, which, in turn, can lead to variations in one or more of the illumination distribution, the shape distribution, the size distribution, the location distribution of the elements of the additional light texture and/or to variations in the number of those elements, as observed by a video camera element (see FIGS. 9 and 10 and the related discussion below). Said variations are captured, at least in part, by the video camera element in a set of video frames which are processed by a computing element according to a method of the present invention to result in a set of numeric values (referred to as the "ALT data" below) which is further processed to obtain numeric values representative of the information related to said at least one physiologic parameter of the person and/or to display at least a part of the set of numeric values using a graphical representation such as a 2D plot.

Application of the additional light texture can greatly increase illumination contrast in the scene observed by a video camera, especially in low ambient light environment such as the one typically present during nighttime. As we demonstrate below, the additional light texture can play the role of an amplification medium for small body movements and its application to a person's body can lead to orders of magnitude increase in the ALT data components related to the heart activity and/or respiration of the person compared to the case when there is no additional light texture present (e.g. when the ALT-generating light element is switched off) during the otherwise equivalent data collection and data processing procedures (see FIGS. 3A-C and the related discussion below).

The additional light texture created by a light source element can cover parts of the objects which are in contact (direct or via other objects) with the person's body (e.g. a chair, a blanket, a bed, floor, etc.) and movements or variations in the shape of such objects resulting from the movements of the person's body imparted to them can be picked up in the ALT data too if said objects are observed by a video camera element. This is why systems and methods according to the present invention can be used to detect heartbeats and respiration events even when a person is completely hidden under a thick quilt, as we show below (see FIGS. 4A-B and the related discussion below).

The light source element, the video camera element, and the computing element of a system according to the present invention may be or may be not housed in a common enclosure. Further, each of said elements can also be a part, physically and/or functionally, of a device or a system other than a system according to the present invention. For example, a processing unit of a laptop computer (computing element), an infrared (IR) camera of an Intel RealSense R200 unit (Intel Corporation, U.S.) embedded into said laptop computer or externally connected to said laptop computer (video camera element), and the IR projector of said R200 unit (light source element) would form a system according to the present invention when, in combination, they perform the function of obtaining information related to at least one of said physiologic parameters according to a method of the present invention.

In one embodiment of a system according to the present invention (referred to as "the first embodiment" below), the light source element is the infrared projector of a Microsoft Kinect for Xbox 360 system (Microsoft Corporation, U.S.), the computing element is a Raspberry Pi single-board computer (Raspberry Pi Foundation, UK), and the video camera element is a Pi NoIR camera (Raspberry Pi Foundation, UK) connected to the Raspberry Pi single-board computer. Though the first embodiment can operate in virtually any lighting environment, an optical band pass filter which matches wavelengths of the Kinect projector can be used with the Pi NoIR camera to reduce effects of fast (relative to the duration of a heartbeat or an inhale/exhale sequence) large-amplitude ambient light intensity variations such as the ones produced by incandescent light bulbs (at e.g. 60 Hz in the U.S.), especially if the incandescent light bulbs are the only source of light for a scene.

In one implementation of a method according to the present invention (referred to as "the first method" below), the following steps are performed:

The infrared projector of the Microsoft Kinect for Xbox 360 system projects a set of light spots onto the objects of a scene, including the body of a person, observed by the Pi NoIR camera, thus adding artificial light texture to the objects of the scene observed by the Pi NoIR camera. The infrared projector of the Microsoft Kinect for Xbox 360 system is turned on or off by the Raspberry Pi single-board computer.

Further, video encoding for the video frames captured by the Pi NoIR camera into H.264 format (see, for example, reference 1 in the list of references below) is performed using the Raspberry Pi single-board computer and functionality provided by Picamera library (documentation for the library is available at picamera.readthedocs.io).

Further, a set of the sum of absolute differences (SAD) numeric values (see, for example, reference 2 in the list of references below) is obtained for (ideally) each of the encoded video frames from the motion vector data generated by the H.264 video encoder for each of the encoded video frames using the Raspberry Pi single-board computer and functionality provided by Picamera library. According to the reference 2, "In digital image processing, the sum of absolute differences (SAD) is a measure of the similarity between image blocks. It is calculated by taking the absolute difference between each pixel in the original block and the corresponding pixel in the block being used for comparison. These differences are summed to create a simple metric of block similarity, the $L^1$ norm of the difference image or Manhattan distance between two image blocks".

Further, a sum of the SAD values in the SAD values set is calculated to obtain a numeric value referred to as the "sSAD" value below using the Raspberry Pi single-board computer for each of the encoded video frames for which SAD values set was obtained. sSAD values form a set of the ALT data values referred to above.

Python code which runs on a Raspberry Pi single-board computer having a Pi NoIR camera connected to it and implements the video frames capture and processing steps described above can be found in the LISTING 1 below.

The computed sSAD values contain information about the respiration and/or heartbeats and/or other mechanical movements of a person observed by the Pi NoIR camera over the time period covered by the encoded video frames. Numeric values representative of the respiration rate and/or heart rate of the person over that time period can be obtained, for example, by performing Fourier analysis (see, for example, reference 3 in the list of references below) of the sSAD values (see FIG. 2 and the related discussion below). Numeric values representative of the heart rate variability and/or respiration rate variability can be obtained, for example, by identifying positions of the peaks corresponding to the heartbeats and/or the respiration events in the sSAD data, determining duration of the time intervals between the successive heartbeat and/or respiration peaks to result in a series of the time interval duration values for the heartbeats and/or respiration, and performing statistical calculations for the obtained series of the time interval duration values, e.g. producing a histogram of said time interval duration values and/or determining parameters such as mean and standard deviation values of the distribution of said interval duration values, in order to thus obtain information about the variation of said time interval durations over the time period covered by said encoded video frames.

As a practical starting point, the Kinect system can be placed at approximately 5 feet distance from a person with the Pi NoIR camera placed in the vicinity of the Kinect. The distance between the Kinect and the person can affect how pronounced the heartbeat signal will be during respiration events (see FIGS. 1 and 5A, 13A-B, and 14A-B, and the related discussion below). At a large enough distance between the Kinect and the person there will be virtually no discernable pulse and/or respiration signal in the ALT data. Generally, the closer Kinect gets to the person, the less pronounced the heartbeat signal component in the ALT data becomes during respiration events. Adjustments of the Kinect and the camera positions can be made, for example, based on observing visualizations of the collected ALT data.

Note that there were essentially no movements of a person's body other than the ones related to the person's respiration and heartbeats during collection of the data shown in all FIGS. discussed below.

An example of the ALT data captured by the first embodiment of a system and the first method according to the present invention described above is shown in FIG. 1. ALT data collection was performed during daytime at 49 data points per second rate (which corresponds to 49 frames per second video capture setting for the Pi NoIR camera, see LISTING 1 below) with simultaneous HD video (720p) recording (see LISTING 1 below). The video frame size was set to 1280×720 pixels (see LISTING 1 below). A person was at 1.5 meters (5 feet) distance from the Pi NoIR camera. The camera observed ⅔ of the person's body. The H.264 video encoder produced I-type and P-type video frames at a ratio of 1 I-type video frame followed by 59 P-type video frames in this example. Motion vector data for I-type video frames and, consequently, sSAD values for I-type video frames are zero. Zero sSAD value of each I-type video frame was replaced by sSAD value of the preceding P-type video frame in the sSAD data shown in FIGS. 1, 4A, 5A, 8A, and 8B. H.264 video encoder can be instructed to produce a single I-type video frame followed by P-type video frames only by setting the appropriate parameter for its operation (see LISTING 1 below).

Figure 1:
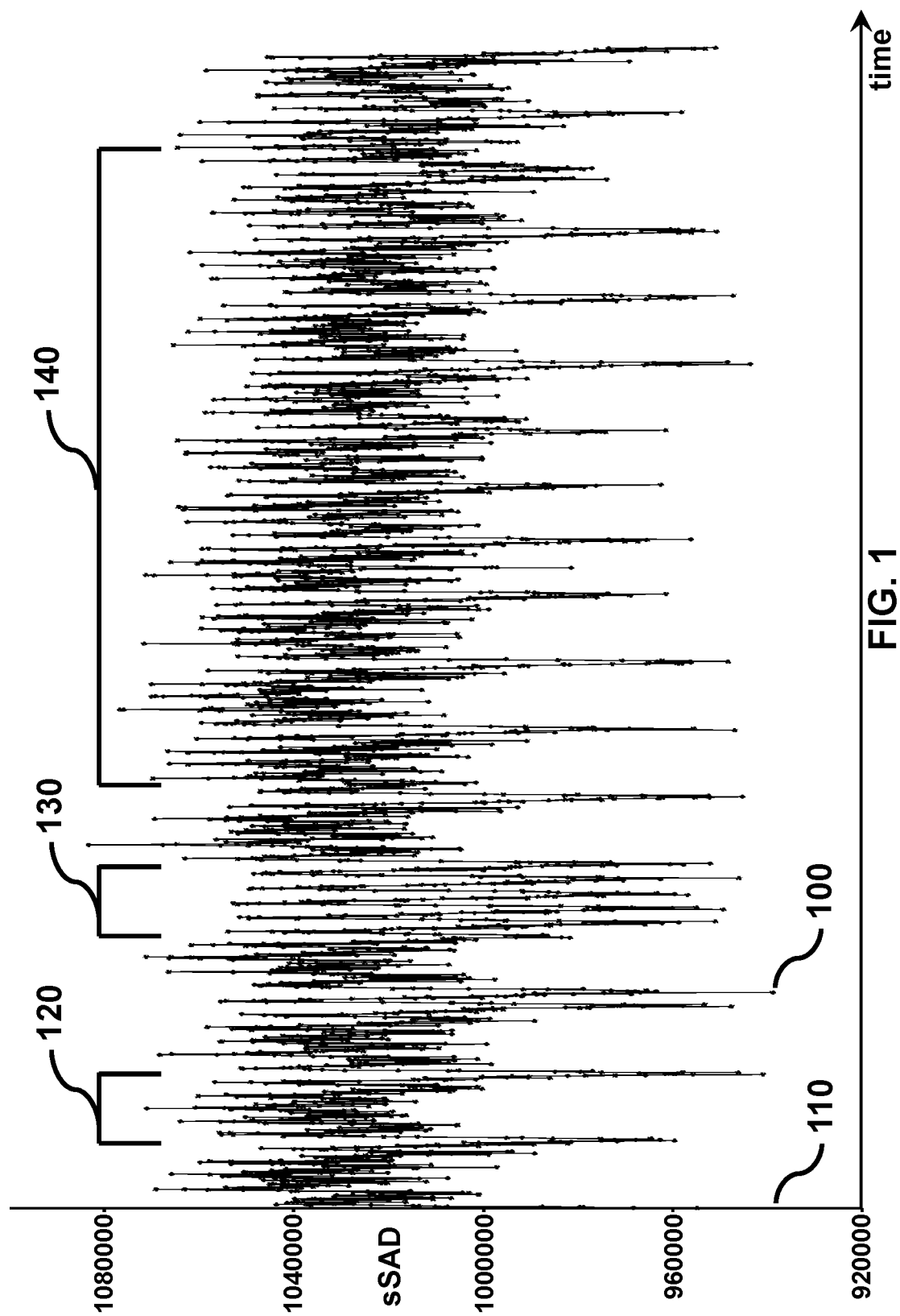
FIG. 1 shows data obtained according to an embodiment of a system and a method of the present invention.

Each data point 100 in FIG. 1 represents the sSAD value for an encoded video frame. The sSAD values can be determined using the vertical axis 110 in FIG. 1. The time progression in FIG. 1 is from left (earlier-captured frames) to right (later-captured frames). The sSAD value data points are connected by straight lines in FIG. 1. The region 120 of the sSAD values in FIG. 1 approximately corresponds to one respiration cycle of the person (inhale followed by exhale). The sSAD values in the region 120 in FIG. 1 reflect both the person's respiration and heartbeats. The region 130 of the sSAD values in FIG. 1 corresponds to a time interval when the person did not breathe. The sSAD values in the region 130 in FIG. 1 reflect the person's heartbeats only.

Figure 2:
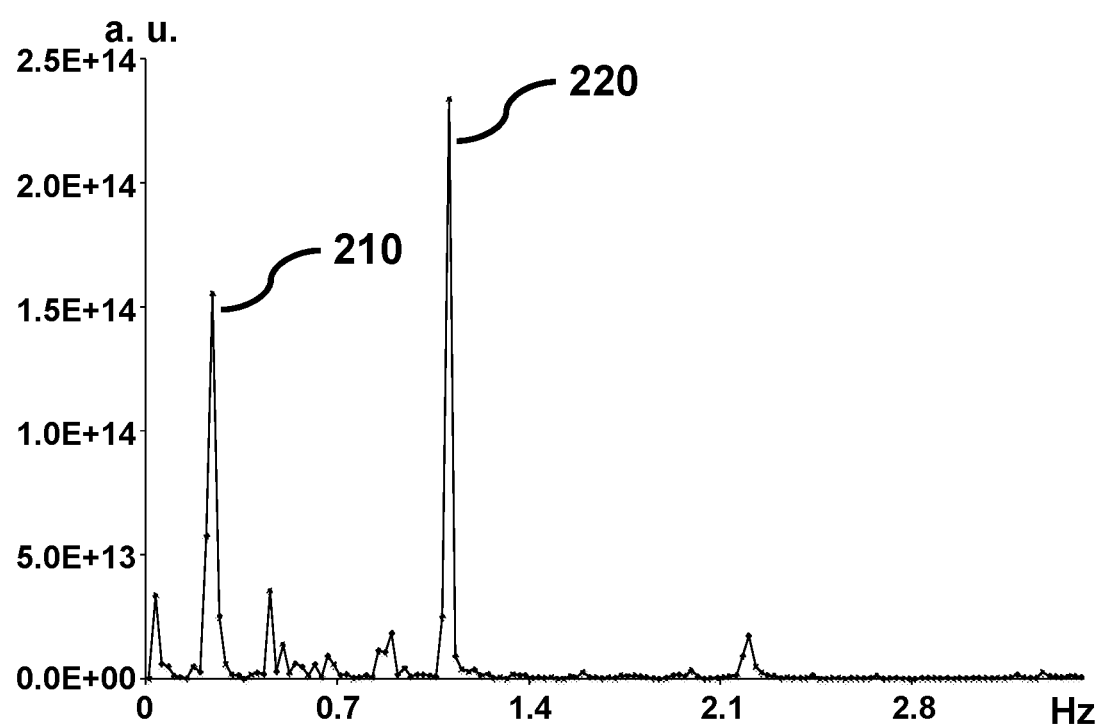
FIG. 2 shows the result of a fast Fourier transformation for a part of the data shown in FIG. 1.

Region 140 in FIG. 1 containing 2048 sSAD data points was used to produce the frequency spectrum shown in FIG. 2. Time duration of the interval 140 in FIG. 1 is approximately 42 seconds. The average value of the sSAD data points in the region 140 in FIG. 1 was subtracted from each of the sSAD values in the region 140 in FIG. 1 followed by application of fast Fourier transform (FFT) to thus obtained average-corrected sSAD values. Frequency peaks 210 (0.24 Hz) and 220 (1.12 Hz) in FIG. 2 correspond to the respiration rate and the heart rate of the person during the interval 140 in FIG. 1, respectively. The frequency values for the peaks 210 and 220 in FIG. 2 correspond to the equivalent values of 14 respiration cycles per minute and 67 heartbeats per minute, respectively.

Figure 3A:
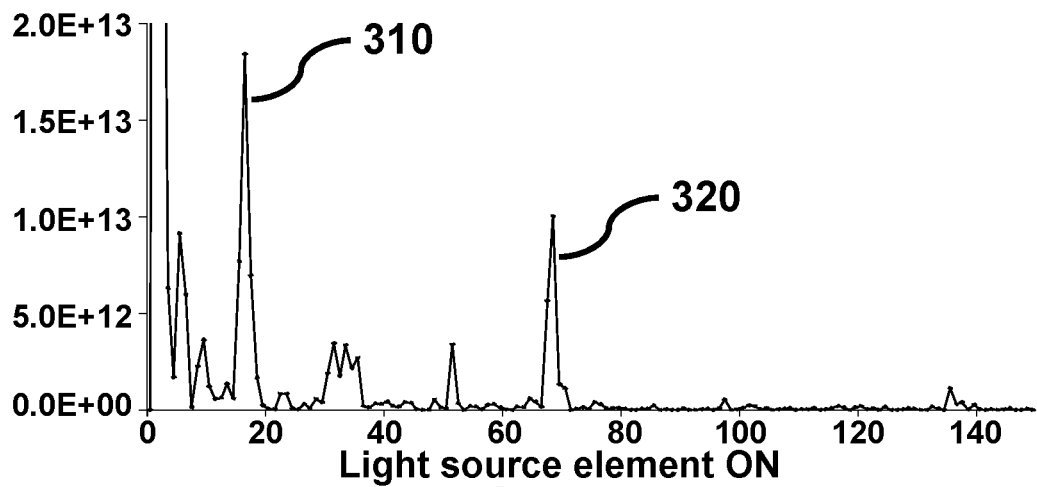
FIGS. 3A-C show that application of the additional light texture to the surfaces of a person's body by a system according to the present invention leads to a significant (at least 100 times in the case shown in FIGS. 3A-C) increase of the spectral components related to the respiration and heart activity of a person.
Figure 3B:
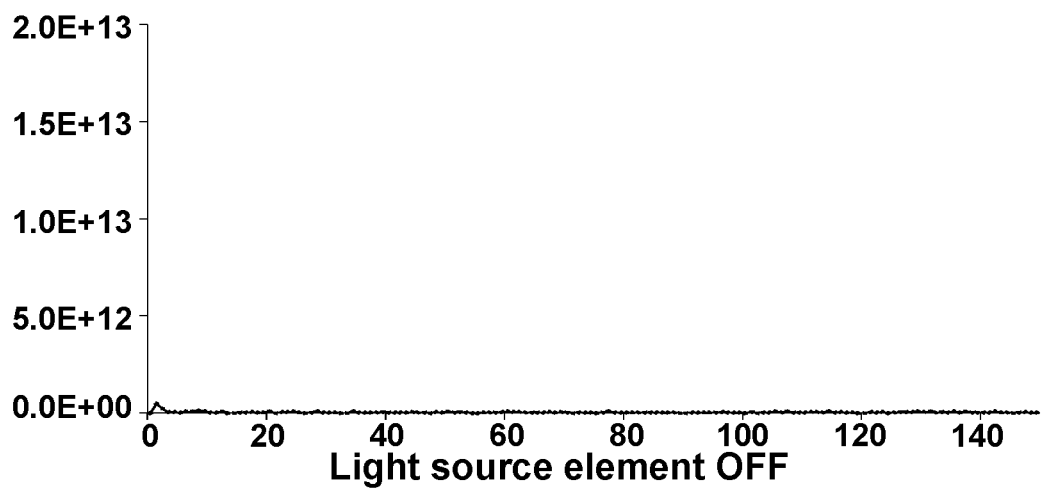
Figure 3C:
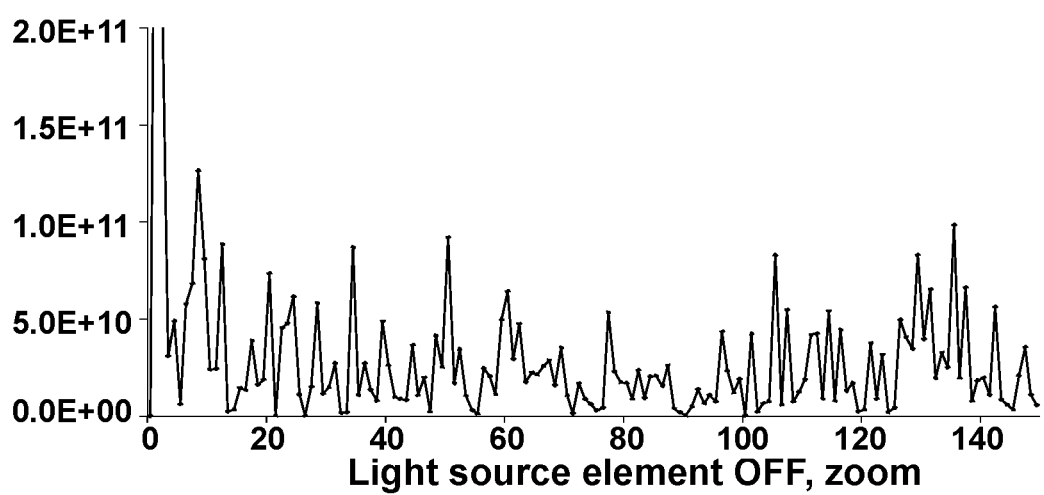

To demonstrate the amplification function of the additional light texture, ALT data collection was performed using the first embodiment of a system and the first method according to the present invention described above during daytime at 90 data points per second rate (which corresponds to 90 frames per second video capture setting for the Pi NoIR camera). The video frame size was set to 640×480 pixels. A person was at approximately 1.3 meters (4.3 feet) distance from the Pi NoIR camera. The camera observed about ½ of the person's body. FIGS. 3A and 3B show frequency spectra which were obtained in the same way as the one in FIG. 2, via fast Fourier transformation of a sSAD values data set. The sSAD data sets used to obtain spectra shown in FIGS. 3A and 3B had the same length and corresponded to one minute data collection time. Said sSAD data sets were collected under the same ambient lighting conditions in the room (the ones excluding the additional illumination created by a light source element). Light emitter of a Microsoft Kinect for Xbox 360 unit was active (switched ON) during collection of the sSAD data set corresponding to FIG. 3A, and said light emitter was inactive (switched OFF) during collection of the sSAD data set corresponding to FIG. 3B. Note that the vertical scales of the plots in FIGS. 3A and 3B are the same. FIG. 3C shows the same data as FIG. 3B, yet the maximum value of the vertical axis in FIG. 3C is one hundred times smaller compared to the maximum values of the vertical axes of the plots in FIGS. 3A and 3B (2.0E+11 for the plot in FIG. 3C vs. 2.0E+13 for the plots in FIGS. 3A and 3B). Therefore, the frequency components 310 and 320 corresponding to respiration and heartbeats of a person, respectively, in the spectrum shown in FIG. 3A are at least one hundred times larger compared to the frequency components in the same regions of the frequency spectra shown in FIGS. 3B and 3C. Horizontal axis numbers of the plots in FIGS. 3A, 3B, and 3C correspond to the frequency bin numbers of the FFT.

Therefore, the data shown in FIGS. 3A, 3B, and 3C demonstrate that application of the additional light texture leads to at least two orders of magnitude amplification of the frequency components corresponding to a person's respiration and pulse in the frequency spectra compared to the case when there is no said additional light texture present.

Note that both respiration rate and heart rate were determined from the same sSAD data.

Note that the "baseline" of the sSAD values can be in the range of hundreds of thousands (see e.g. FIG. 1) while the heartbeats/respiration/other movements signal can have just several percent amplitude relative to the baseline even when the artificial light texture is applied to a person's body.

FIGS. 4B, 5B, 7, 9, and 10 show the images captured by a Pi NoIR camera which were converted to grayscale images.

To demonstrate that systems and methods according to the present invention can be used to detect heartbeats and respiration even when a person is completely covered by a thick blanket, ALT data collection was performed using the first embodiment of a system and the first method described above during nighttime at 49 data points per second rate (which corresponds to 49 frames per second video capture setting for the Pi NoIR camera). The video frame size was set to 1280×720 pixels.

Figure 4A:
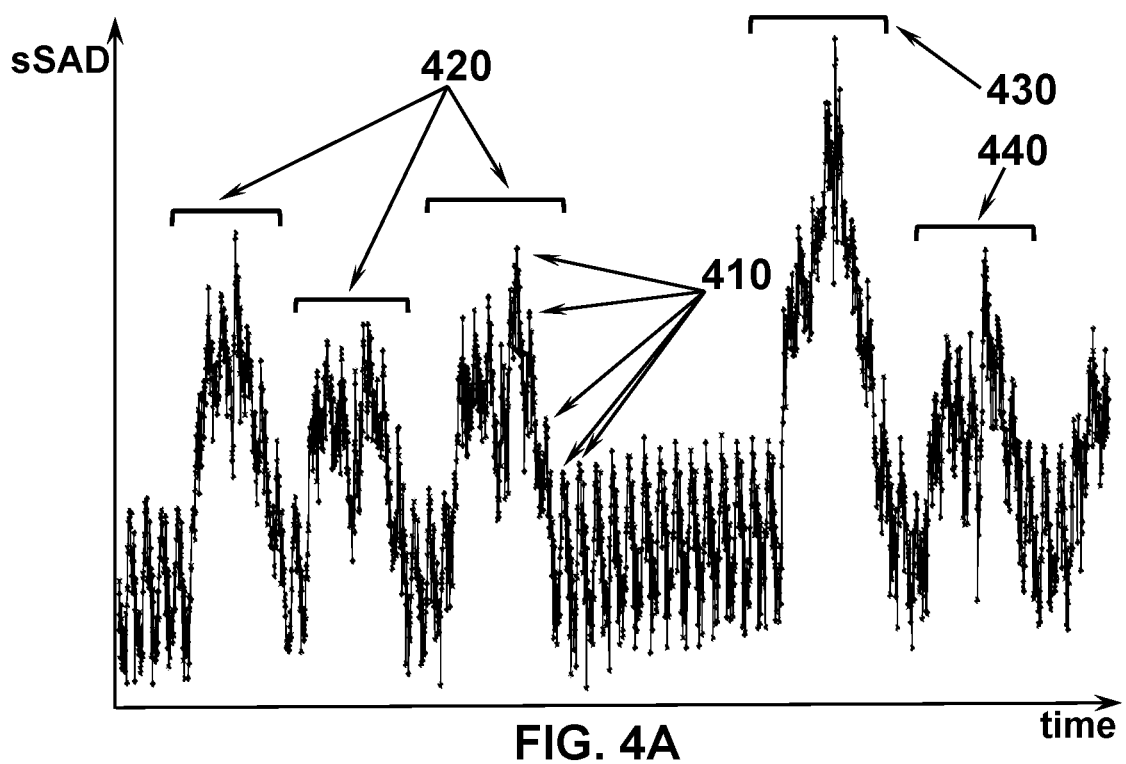
FIGS. 4A-B show that systems and methods according to the present invention can be used to detect heartbeats and respiration of a person even when the person is completely covered by a thick quilt.
Figure 4B:

FIG. 4B shows a person reclining in an armchair and completely covered by an "IKEA 365+MYSA" quilt having "warmth rate" 6 ("thick and heavy" quilt, 150×200 cm, 1730 g filling weight). The room in FIG. 4B was almost totally dark for a human eye because human eyes are mostly insensitive to the infrared light near the wavelength on which Kinect projector operates. The remnant illumination in the room, which could be noticed by a person, was due to the distant streetlights and LEDs of the electronics equipment in the room. Note that ALT works in daylight too, as data in FIGS. 1-3 demonstrate.

FIG. 4A shows ALT data collected for the person under the quilt in FIG. 4B. Duration of the dataset in FIG. 4A is about one minute. Both respiration and pulse signals are pronounced in FIG. 4A. Several of the consecutive heartbeats are marked by the arrows 410 in FIG. 4A. Each of the five regions of the ALT data under the brackets marked by the arrows 420, 430, and 440 corresponds to a respiration cycle (inhale followed by exhale). Note that there was breath hold between the respiration cycles 420 and 430 and that the person made a fast inhale during the respiration cycle 430 following the breath hold, which is reflected in the rate of change and the amplitude of the ALT data for that cycle in FIG. 4A.

Figure 5A:
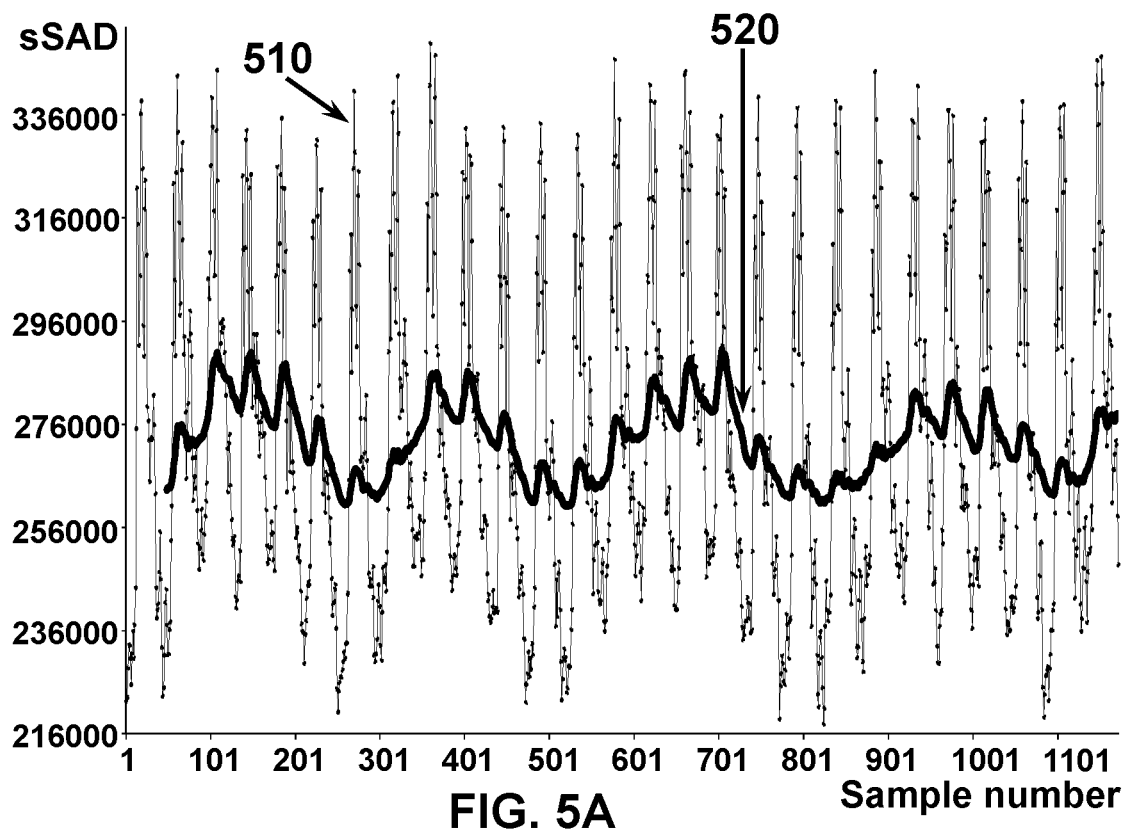
FIGS. 5A-B show that systems and methods of the present invention can be used to detect heartbeats and respiration of a sleeping person during nighttime.
Figure 5B:

FIG. 5B shows an image of a person sleeping under a blanket on a bed during nighttime. A Pi NoIR camera captured the image. FIG. 5B shows the light spots produced by the light emitter of a Kinect for Xbox 360 unit which accounted for the majority of illumination for the scene observed by the Pi NoIR camera. The light spots formed distinct illumination areas, the elements of the artificial light texture created by said light emitter. The elements of the artificial light texture shown in FIG. 5B will be discussed in more detail below (see FIG. 10 and the related discussion below). Both the Pi NoIR camera and the Kinect unit were at about ~2.3 m (7.5 feet) minimum distance (the distance to the closest point of the person's body) from the person in this case.

The ALT data shown in FIG. 5A were collected using the first embodiment of a system and the first method according to the present invention described above at 49 samples per second rate. The frame size of the video captured by the Pi NoIR camera was set to 1280×720 pixels. Thin black lines 510 in FIG. 5A connect the sSAD data points. ALT data in FIG. 5A reflect both respiration and heartbeats of the person. Further, a 49-points moving average was calculated for the sSAD values shown in FIG. 5A to highlight the respiration process captured in the ALT data. The thick black line 520 in FIG. 5A goes through the points which are the result of said moving average calculations and shows that there were four full respiration cycles captured in the ALT data shown in FIG. 5A. There were a total of 27 heartbeats captured in the ALT data shown in FIG. 5A.

As discussed above, application of the additional light texture can greatly increase illumination contrast in the scene observed by a video camera, especially in a low ambient light environment such as the one typically present during nighttime. FIG. 5B illustrates this statement well. Without the illumination produced by the Kinect's light emitter FIG. 5B would be (almost) uniformly pitch-black.

If, for example, n is the number of bits used to represent the shades of gray in a grayscale image such as the one in FIG. 5B, than the minimum ratio, other than 1, of grayscale values of the pixels belonging to two areas of a person's body in the image which reflects the ratio of the illumination of the body areas covered by said pixels in the image is $1+1/(2^n-2)$. If n=16, said ratio is about 1.000015. The ratio of said pixel values can be used as a measure of the illumination contrast between the different parts of the video frame captured by a video camera element. If a light source element, such as the one used in the first embodiment of a system according to the present invention described above, is the only or the major source of illumination for a scene observed by a video camera element (as is the case for FIGS. 4B and 5B), video frames captured by the video camera element will have areas with vastly different illumination, and hence large values of the illumination contrast between those areas (e.g. $2^n-1$ between the pixels having the minimum non-zero grayscale level value of 1 and the maximum grayscale level value of $2^n-1$; said ratio is 65535 for n=16, for example), as compared to the case when the scene observed by the video camera element has no illumination in it (e.g. when the light source element is switched off; we assume that the minimum grayscale level value for any pixel in a grayscale image is 1 to avoid considering "divide by zero" operations).

Note that a light source which provides substantially uniform illumination of the scene as observed by a video camera element (compared to the illumination created by a light source element which creates the additional light texture) can be used in addition to the light source element which creates the additional light texture, if, for example, such added substantially uniform illumination can aid a person to see the elements of the scene as captured in the video frames by the video camera element better compared to the case when the light source element which creates the additional light texture is the main or the only source of illumination for a scene, as is the case for FIG. 5B, for example.

Note that there is no calculation of the lengths of the motion vectors form the motion vector data generated by a video encoder (such as H.264 one) for a video frame captured by a video camera element in the methods according to the present invention. Instead, a simple integral measure of motion in the video frame is used which is based on the computation of the sSAD value. Other integral measures for the amount of motion in a video frame which are based on calculation of a sum of absolute values of numeric values associated with the pixels of a video frame captured by a video camera element are possible. For example, one can calculate absolute values of the motion vector components generated by a video encoder for a macroblock of the video frame (the components of said motion vector are referred to as the X-component and Y-component) and find a sum of said absolute values of the motion vector components for all the macroblocks of the video frame. Such measure of motion is referred to as XYabs below.

Figure 6:
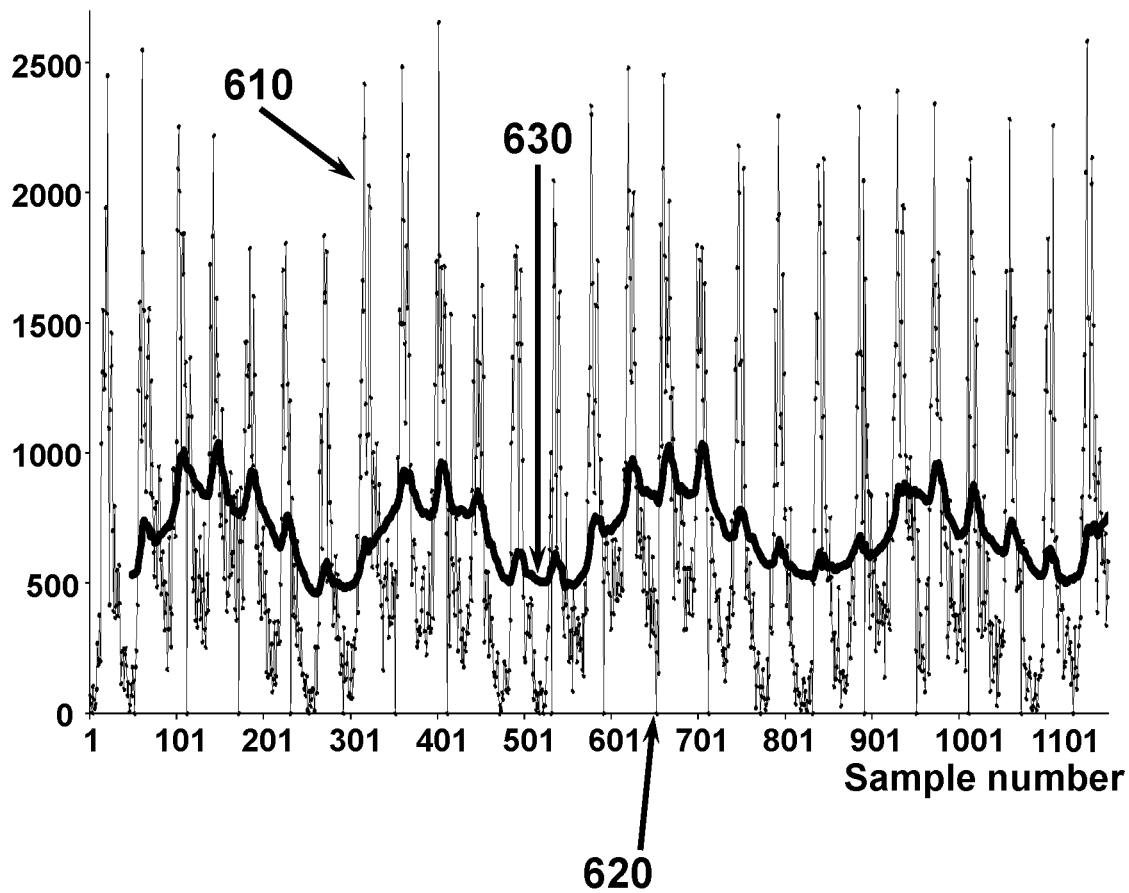
FIG. 6 shows data obtained using an implementation of a method according to the present invention.

FIG. 6 shows the XYabs values computed for the same video frames which were used to produce sSAD data shown in FIG. 5A. Lines 610 in FIG. 6 connect XYabs data points. Similarly to the sSAD values for the I-type video frames, XYabs values for the I-type video frames are equal to zero. XYabs value (zero) for one of the I-type video frames from the video frames set used to generate the data for FIGS. 5A and 6 is indicated in FIG. 6 by the arrow 620. Similarly to FIG. 5A, a 49-points moving average was calculated for the XYabs values to highlight the respiration process captured in the ALT data. The thick black line 630 in FIG. 6 goes through the points which are the result of said moving average calculations and shows that there were four full respiration cycles captured in the ALT data shown in FIG. 6. FIG. 6 shows the same number of heartbeats, 27, as does FIG. 5A.

Figure 7:
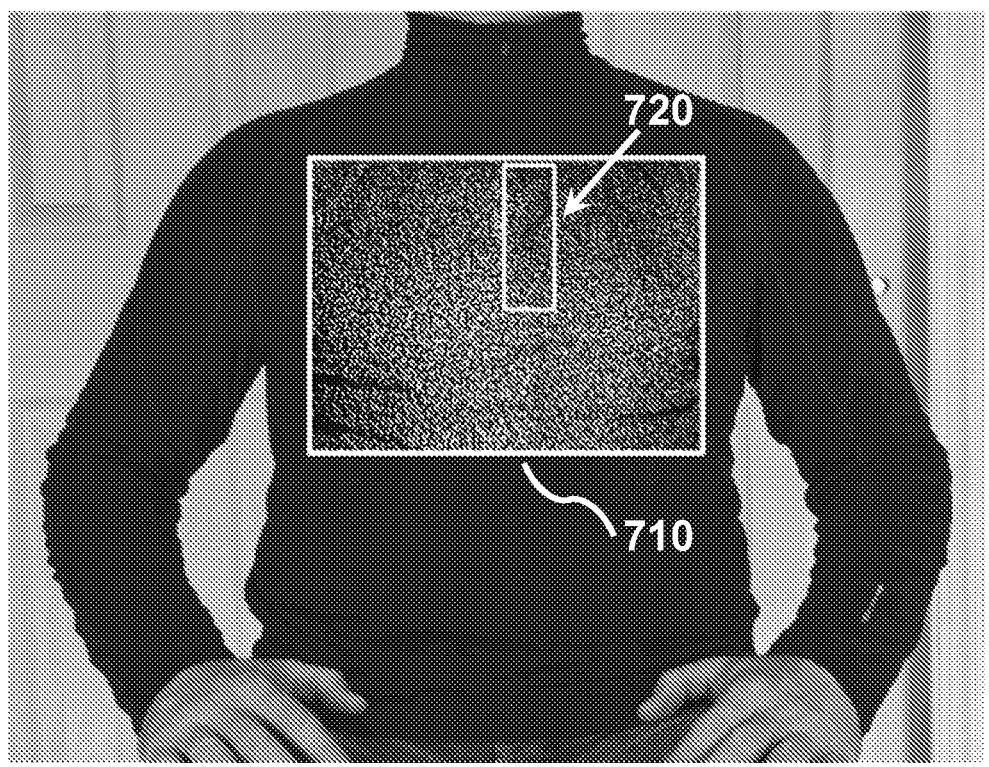
FIG. 7 shows a person sitting on a chair.
Figure 8A:
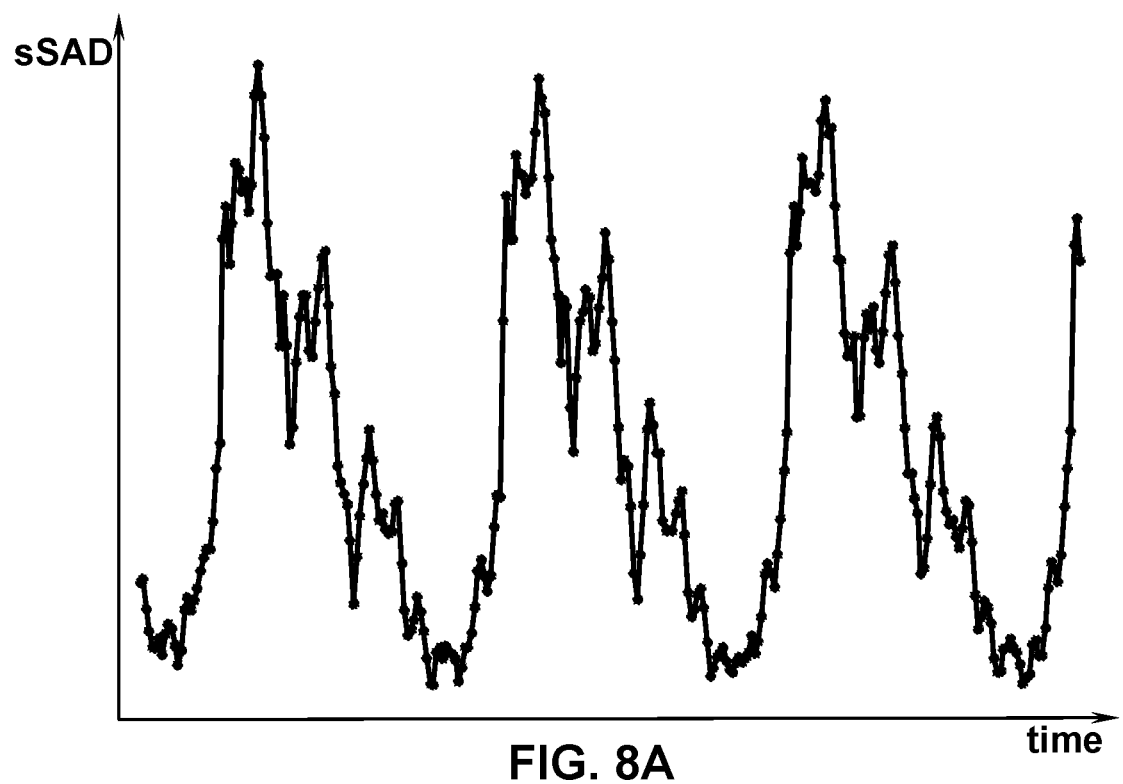
FIGS. 8A-B show that systems and methods of the present invention can be used to obtain temporal profiles of the heartbeats of a person in a non-contact fashion and with high temporal resolution.
Figure 8B:
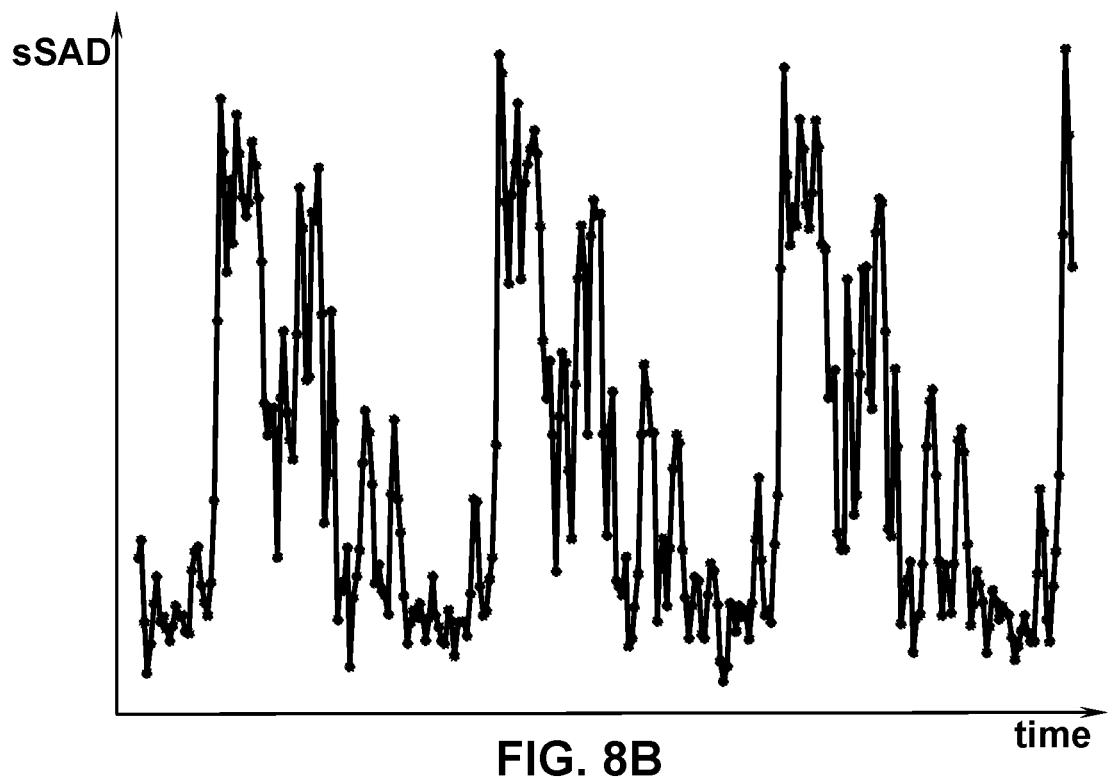

Systems and methods according to the present invention can be used to obtain pulse, respiration, and other mechanical motion information specific to different parts of a person's body simultaneously and with high temporal resolution via processing respective segments of the captured video frames. FIGS. 7, 8A, and 8B show that systems and methods of the present invention can be used for obtaining information about the intricate details of the mechanical movements of a heart in a non-contact fashion. Collection of the ALT data shown in FIGS. 8A and 8B was performed during daytime using the first embodiment of a system and the first method according to the present invention (described above).

FIG. 7 shows a part of the upper body of a person. The rectangle 710 in FIG. 7 surrounds the area observed by a Pi NoIR camera and illuminated by the light emitter of a Kinect for Xbox 360 unit. Note that the part of the image shown in FIG. 7 within the rectangle area 710 was obtained separately from the rest of the image and put on top of said rest of the image to provide a better illustration of the location of the imaged areas of the person's body. The camera's frame size was set to 640×480 pixels. Data in FIGS. 8A and 8B were collected by the Pi NoIR camera running at 90 frames per second rate, which gives 11 milliseconds time interval between the data points, given that the Pi NoIR camera's video capture parameters were fixed during the acquisition of the video frames used to produce sSAD data values shown in FIGS. 8A and 8B (see LISTING 1 below). Both the PiNoIR camera and the Kinect unit were at about 0.6 m (~2 feet) distance from the person when the image in the area 710 and the data shown in FIGS. 8A and 8B were obtained.

FIG. 8A shows ALT data for three heartbeats obtained by processing the whole video frames captured by the Pi NoIR camera (640×480 pixels, corresponds to the rectangle 710 in FIG. 7). The data in FIG. 8B correspond to the same heartbeats which are shown in FIG. 8A. ALT data in FIG. 8B were obtained for the areas around the person's heart marked by the rectangle 720 in FIG. 7 by processing the parts of the whole video frames which correspond to the rectangle 720 in FIG. 7 using the first method of the present invention. Note that the vertical axes in FIGS. 8A and 8B have different scales (not specified).

As FIGS. 8A and 8B demonstrate, the ALT data collected from the small regions close to the person's heart (FIG. 8B) exhibit higher resolution for the details of the heartbeat profile compared to the ALT data for the whole area within the rectangle 710 in FIG. 7 (FIG. 8A).

The data in FIGS. 8A and 8B demonstrate that systems and methods according to the present invention can be used to obtain information specific to different parts of a body via processing different segments of the video frames captured by a video camera element. ALT data collection can be performed with high temporal resolution (11 ms time interval between the data points in FIGS. 8A and 8B, limited by the maximum frame rate of the used video camera element). These capabilities of the systems and methods of the present invention can be valuable for medical imaging applications where tracking pulse, heartbeats, respiration, and other movements is required for the whole body and/or for any number of its specific areas. FIGS. 8A and 8B demonstrate that systems and methods according to the present invention can be viewed as a non-contact analog of the seismocardiography and ballistocardioraphy methods of monitoring the mechanical activity of a heart and a vascular system.

Systems and methods according to the present invention can be used to obtain information related to the temporal characteristics of at least a part of a heartbeat, and temporal characteristics of at least a part of a respiration cycle via, for example, determining temporal positions of the sSAD values maxima relative to a fixed time point or relative to each other, or determining duration of time during which sSAD values are above a certain level or within a certain range of numeric values, or by establishing time dependence of the sSAD values corresponding to at least a part of a heartbeat or at least a part of a respiration cycle.

FIG. 9 shows images 910 and 920 obtained by a system according to the first embodiment of the present invention with the Pi NoIR camera focused on the same area of a person's body which is shown within the rectangle 710 in FIG. 7. The images 910 and 920 were obtained under the same conditions as the one within the rectangle 710 in FIG. 7.

White rectangles 930 and 940 in FIG. 9 surround the areas of the images 910 and 920, respectively, which are shown in the images 970 and 980 in FIG. 9, respectively. Rectangles 930 and 940 have the same position within the images 910 and 920, respectively. The images 910 and 920 have the same dimensions.

As the images 910, 920, 970, and 980 in FIG. 9 show, the light emitter element of the first embodiment of a system according to the present invention illuminates a set of areas of a person's body by creating light spots on those areas, two of those light spots are indicated by the arrows 950 and 960 in FIG. 9. Said light spots generally have arbitrary shapes, as captured by a video camera element, and are separated from each other by the areas of the person's body having lower illumination compared to that of the light spots. Said light spots form the elements of the additional (artificial) light texture produced by the first embodiment of a system according to the present invention.

Image 910 and, consequently, its part 970 were taken in between the heartbeats of the person when the person did not breathe. Image 920 and, consequently, its part 980 were obtained in the middle of a respiration cycle of the person.

As comparison of the images 910 and 920, and of their parts shown in the images 970 and 980 in FIG. 9, respectively, indicates, respiration, heartbeats, and/or other mechanical movements of the person's body lead to variations in the illumination distribution, the shape distribution, the size distribution, the location distribution, and the difference in the number of the elements of the artificial light texture between the images 910 and 920, and between their parts shown in the images 970 and 980 in FIG. 9, respectively. Said variations are captured, at least in part, by a video camera element in a set of video frames which are processed by a computing element according to a method of the present invention to result in a set of numeric values (ALT data) which is further processed to obtain numeric values representative of the information related to said at least one physiologic parameter of the person, as discussed above, for example, and/or to display at least a part of the set of numeric values using a graphical representation such as a 2D plot, as shown in FIGS. 8A and 8B, for example.

FIG. 10 shows images 1010 and 1020 obtained by a system according to the first embodiment of the present invention with the Pi NoIR camera focused on the same scene which is shown in FIG. 5B. The images 1010 and 1020 were obtained under the same conditions as the one in FIG. 5B.

White rectangles 1030 and 1040 in FIG. 10 surround the areas of the images 1010 and 1020, respectively, which are shown in the images 1050 and 1060 in FIG. 10, respectively. Rectangles 1030 and 1040 have the same position within the images 1010 and 1020, respectively. The images 1010 and 1020 have the same dimensions. Rectangles 1030 and 1040 surround the chest and abdomen areas of a person covered by a blanket.

As images 1010, 1020, 1050, and 1060 in FIG. 10 show, the light emitter element of the first embodiment of a system according to the present invention illuminates a set of areas of the person's body by creating light spots on those areas. Said light spots generally have arbitrary shapes, as captured by a video camera element, and are separated from each other by the areas of the person's body having lower illumination compared to that of the light spots. Said light spots form the elements of the additional (artificial) light texture produced by the first embodiment of a system according to the present invention.

Image 1010 and, consequently, its part 1050 were taken in between the heartbeats of the person when the person did not breathe. Image 1020 and, consequently, its part 1060 were obtained during a respiration cycle of the person.

As comparison of the images 1010 and 1020, and of their parts shown in the images 1050 and 1060 in FIG. 10, respectively, indicates, respiration, heartbeats, and/or other mechanical movements of the person's body predominantly lead to variations in the illumination distribution of the elements of the artificial light texture between the images 1010 and 1020, and between their parts shown in the images 1050 and 1060 in FIG. 10, respectively, as compared to variations in the illumination distribution, the shape distribution, the size distribution, the location distribution, and the difference in the number of the elements of the artificial light texture between the images 910 and 920, and between their parts shown in the images 970 and 980 in FIG. 9, respectively. Note that the light source element and the camera element were positioned at a larger distance from the person in the case shown in FIG. 10 (~2.3 m minimum distance) compared to the case shown in FIG. 9 (~0.6 m). Said variations are captured, at least in part, by a video camera element in a set of video frames which are processed by a computing element according to a method of the present invention to result in a set of numeric values (ALT data) which is further processed to obtain numeric values representative of the information related to said at least one physiologic parameter of the person, as, for example, discussed above, and/or to display at least a part of the set of numeric values using a graphical representation such as a 2D plot, as shown in FIGS. 5A and 6, for example.

With respect to the mentioned difference between the responses of the elements of the additional light texture to the mechanical movements of a person's body, including those associated with the person's respiration and heartbeats, shown in FIGS. 9 and 10, consider the case where the light source element and the video camera element are placed at essentially the same location. At large enough distances between the light source and the camera element, on one end, and the person, on the other end, the elements of the additional light texture created by the light source element on the surfaces of the person's body, as observed by the video camera element, are small, occupying a single pixel or a small group of a few pixels in the video frames captured by the video camera element (the first case of the distance, generally corresponds to the cases shown in FIGS. 5B and 10). In the first case of the distance, movements of the person's body, including those associated with heartbeats and respiration, predominantly result in changes in the illumination distribution of the ALT elements, as observed by the video camera element. As the distance between the video camera element, the light source element, on one end, and the person, on the other end, gets smaller, the size and the density of the ALT elements, as observed by the video camera element, increases (the second case of the distance, generally corresponds to the cases shown in FIGS. 4B, 7, and 9). In the second case of the distance, movements of the person's body, including those associated with heartbeats and respiration, generally result in changes in one or more of the position, the shape, the size, the number of the ALT elements in addition to the changes in the illumination distribution of the ALT elements in the video frames captured by the video camera element.

Comparison of the data shown in FIG. 5A (corresponds to the first case of the distance discussed above) and FIGS. 1 and 4A (correspond to the second case of the distance discussed above) indicates that the respiration process becomes more pronounced in the ALT data the smaller the distance between a person and the light source and the camera elements of a system according to the present invention. Increase of the relative contribution of respiration in the ALT data in said second case of the distance compared to said first one indicates that the relative contribution of the changes in the position, and/or the shape, and/or the size, and/or the numbers of the ALT elements associated with respiration into ALT data increases with decreasing the distance between the person and the light source and the camera elements of a system according to the present invention.

Although the patterns of the Kinect-generated light spots (ALT elements) shown in FIGS. 4B, 5B, 7, 9, and 10 are not the patterns of subjective speckles which can be produced by observing a single laser spot, the same interference phenomena which lead to formation of a speckle pattern using a single laser beam and the corresponding spot can contribute to the illumination distribution within each individual element of the additional light texture, as captured by the video camera element, along with the contributions to the illumination distribution within said element due to the geometric (e.g. tilt, curvature) and physical properties of the different parts of the surfaces of a human body.

Some of the other possible embodiments of the systems according to the present invention use Intel RealSense cameras (Intel Corporation, U.S.) and will be discussed below.

Light emitters of RealSense cameras can be used as light source elements for embodiments of the systems according to the present invention. Systems according to the present invention can use RealSense cameras themselves or use another camera such as, for example, a Raspberry Pi NoIR camera as a video camera element for video frames capture.

Systems and methods according to the present invention can work with different types of static light patterns generated by various devices such as Microsoft Kinect for Xbox 360 (see above; see FIGS. 4B, 5B, 7, 9, and 10), and Intel RealSense R200 cameras (see below; see FIGS. 11 and 13A-B; see reference 4 in the list of references below: "Each R200 also includes an infrared texture projector with a fixed pattern . . . . The pattern itself is designed to be a high-contrast, random dot pattern"). Systems and methods according to the present invention can also work with dynamically projected patterns, as the ones generated by Intel RealSense F200 cameras (see below; see FIGS. 12 and 14A-B; see reference 5 in the list of references below).

Note that the common feature of such different types of light patterns which can be used by the systems of the present invention and according to the methods of the present invention is illumination of a set of areas of a person's body, said illumination leads to creating or increasing illumination contrast between said areas and the other areas of the person's body, as observed in the video frames captured by a video camera element (the illumination contrast can be measured, for example, using video frame data as discussed above). Said illumination creates elements of the additional light texture. As discussed above, movements of the person's body, including those which are related to the person's respiration and/or heartbeat, can lead to variations in one or more of the illumination distribution, the shape distribution, the size distribution, the location distribution of the elements of the additional light texture and/or to variations in the number of those elements, as observed by a video camera element (see FIGS. 9 and 10 and the related discussion above). Said variations are captured, at least in part, by the video camera element in a set of video frames which are processed by a computing element according to a method of the present invention to result in a set of numeric values (referred to as the "ALT data") which is further processed to obtain numeric values representative of the information related to said at least one physiologic parameter of the person and/or to display at least a part of the set of numeric values using a graphical representation such as a 2D plot.

As we have discussed above, one of the possible implementations of a method according to the present invention includes obtaining sum of absolute differences (SAD) numeric values generated by a video encoder for the video frames captured by a video camera. Alternatively to using a video encoder data, calculation of the sum of absolute differences numeric values can be incorporated in the methods according to the present invention in other ways, as we describe, for example, below.

As a possible implementation, SAD-generating computations can include iterating over pixels of a given captured video frame, for each pixel of the video frame calculating a difference between a numeric value of a certain kind associated with that pixel in the video frame data (e.g. the value corresponding to the pixel's grayscale level) and a numeric value associated with the corresponding pixel of another captured video frame, calculating the absolute value of the found difference, and adding the calculated absolute value to the sum of the absolute values calculated on the previous step of the iteration process. The sum of absolute differences numeric value (referred to as the "mSAD" value) thus computed for a given video frame is analogous to the sSAD value obtained from the data generated by a video encoder. Two pixels belonging to different video frames can be designated as corresponding to one another if these pixels are located in the same pixel row and in the same pixel column within the video frames; other rules can be used to designate the corresponding pixels; the corresponding pixels can occupy different pixel rows and/or different pixel columns within the video frames.

The mSAD value computed for a captured video frame, as described above, is a simple metric of the similarity between that video frame and another video frame (called the "reference" video frame) which data were used in the computation of the mSAD value. The mSAD value is the "Manhattan distance" (see, for example, reference 6 in the list of references below) between the two video frames computed using numeric values associated with the video frame pixels.

Similarly, SAD value generated by a video encoder (e.g. H.264 one) for a macroblock (see, for example, reference 7 in the list of references below) of a video frame, which we have used above, is a measure of similarity between the macroblock and the corresponding macroblock of another video frame (the reference video frame), the "Manhattan distance" between these two macroblocks. Therefore, sSAD value can be viewed as "Manhattan distance" between two video frames computed using video encoder-generated data.

Similarly to the mSAD value computation described above, SAD value generated by a video encoder for a macroblock of a video frame can be obtained by calculating for each pixel of the macroblock the absolute difference between a numeric value associated with the pixel and a numeric value associated with a pixel of the corresponding macroblock of the reference video frame, and finding a sum of these absolute difference values.

Note that the corresponding macroblocks (the correspondence between the macroblocks is established by a video encoder) can generally have different position within the video frames. Two pixels used in the absolute value calculation can have different position within the video frames too in an implementation of a method according to the present invention whether it uses data generated by a video encoder or not.

For an implementation of a method according to the present invention, the numeric value associated with a pixel of a video frame can be taken directly from the video frame data for the pixel (e.g. pixel's grayscale level) or obtained as a result of calculations using one or more of the video frame data values for the pixel and/or other pixels of the video frame (e.g. an average of the grayscale level values for the pixel and all of its neighboring pixels in the video frame).

Note that although for any captured video frame the methods according to the present invention typically use the one immediately preceding it as the reference video frame in the SAD and/or sSAD and/or mSAD values computations, any one of the captured video frames can be used as the reference video frame for any other captured video frame for the data generation purposes according to the methods of the present invention.

Moreover, by letting the reference video frame to be separated from a given video frame in the video frames set by one or more video frames one can obtain mSAD data, for example, corresponding to different timescales or different effective frame rates. For example, video frames capture done at 100 frames per second rate (typically referred to as "fps"), which corresponds to 10 ms time interval between the consecutive video frames given the fixed camera settings such as exposure duration (see LISTING 1), for 30 seconds results in a video frames set having 3000 video frames. One can process video frames in this set by selecting for each video frame for which mSAD value is to be obtained the immediately preceding one as the reference video frame to produce mSAD data corresponding to 10 ms time interval between the video frames or 100 frames per second capture rate. One can form a sub-set of the collected set of the video frames by selecting each $10^{th}$ video frame of said set. mSAD data obtained by processing said sub-set of the video frames by selecting for each video frame for which mSAD value is to be obtained the immediately preceding one in the sub-set as the reference video frame will correspond to 100 ms time interval between the mSAD data points or to the effective 10 frames per second rate.

Respiration, heartbeats and/or other movements of a person's body cause additional variations of the "Manhattan distance" between the captured video frames compared to the case when there are no body movements (and/or body-caused movements of the other objects) in the scene. Thus, the computed sSAD and/or mSAD values, both of which represent the "Manhattan distance" between the captured video frames, contain information about the respiration and/or heartbeats and/or other movements of a person over the time period covered by the captured video frames.

Application of the artificial light texture to a person's body and/or to the objects surrounding the person can lead to significant enhancement of the variations in the "Manhattan distance" between the captured video frames which (the variations) are associated with the respiration and/or heartbeats and/or other movements of the person compared to the case when the artificial light texture is absent (e.g. when the ALT-generating light emitter is switched off) and otherwise identical data collection and data processing steps are performed.

Provided that video frames are captured at equal time intervals, the computed sSAD and/or mSAD values can be viewed as the integral of (the sum of) the rate of change of the numeric values which are associated with the video frame pixels and used in the sSAD and/or mSAD values computations.

Note that the methods according to the present invention can use mSAD and/or sSAD values irrespective of the type of the additional light texture created by the systems according to the present invention.

Note that the main reason for using the absolute value of the difference between two numeric values associated with the pixels of the video frames in the implementations of the methods of the present invention described above is that we are interested in the amplitude of the change between said values rather than in the sign (positive vs. negative) of said change. Therefore, the absolute value calculation operation can be replaced by another operation which has the same effect of providing information about the magnitude rather than the sign of the change between the numeric values associated with the pixels of the video frames in other implementations of the methods of the present invention. For example, one can perform calculation of the squared value of the difference, difference$^2$, instead of calculating its absolute value, 'difference', in an implementation of a method according to the present invention.

Figure 11:
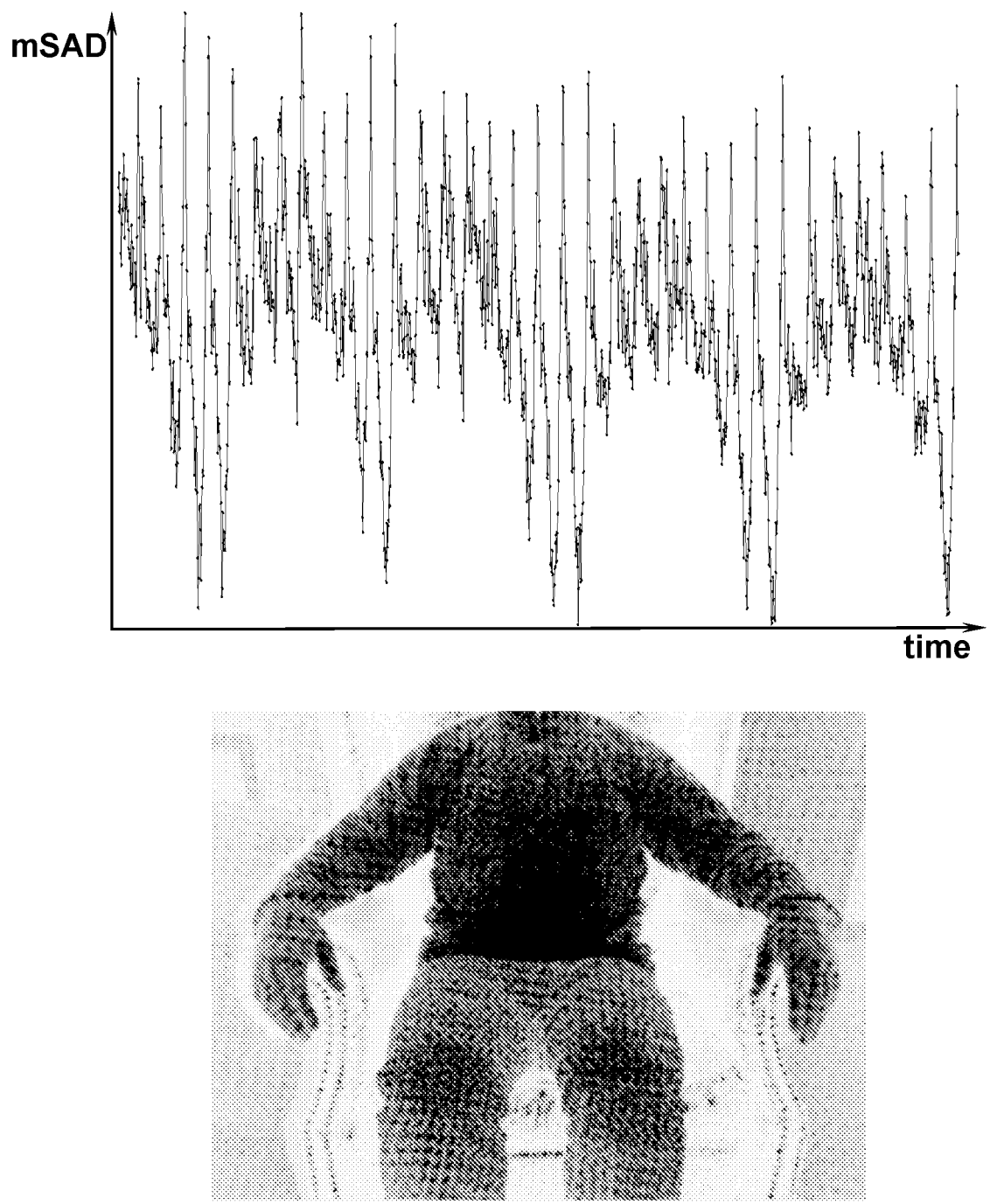
FIG. 11 shows data obtained using an embodiment of a system and an embodiment of a method according to the present invention.
Figure 12:
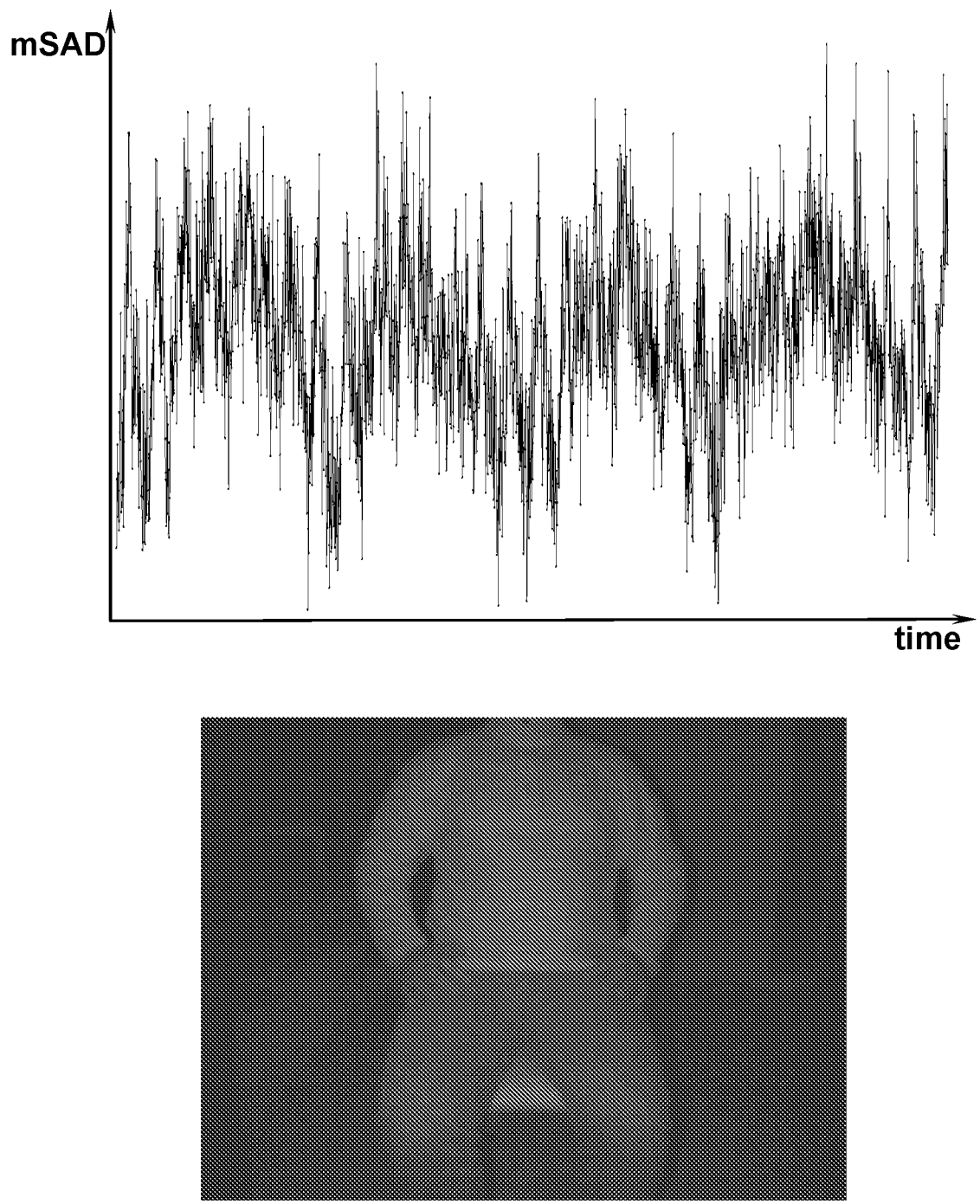
FIG. 12 shows data obtained using an embodiment of a system and an embodiment of a method according to the present invention.

The raw mSAD ALT data are shown in the FIGS. 11, 12, 13A-B, and 14A-B by lines connecting the data points (the computed mSAD values for the captured video frames shown by dots). Snapshots of the scene captured by the video camera elements are shown below the corresponding data plots in FIGS. 11 and 12. Two pixels which were designated as corresponding to one another in the computations of the mSAD values shown in FIGS. 11, 12, 13A-B, and 14A-B were located in the pixel rows having the same number and in the pixel columns having the same number within two different video frames used for a mSAD value computation. We used grayscale level of a pixel as the numeric value associated with the pixel in mSAD values computations. Also, for any given video frame we used the one immediately preceding it as the reference video frame for computations of the mSAD values shown in FIGS. 11, 12, 13A-B, and 14A-B.

mSAD data in FIG. 11 were obtained using the light emitter and IR video stream of a R200 Intel RealSense camera running at 60 frames per second rate. A snapshot of the scene taken from the R200 IR video stream is shown below the mSAD data plot in FIG. 11. A person is sitting in an armchair at about 3 feet distance from the R200 camera. mSAD data in FIG. 11 captured four full respiration cycles of the person. Numeric values for the heart rate and respiration rate, for example, can be obtained, for example, via Fourier analysis of the mSAD data.

mSAD data in FIG. 12 were obtained using the light emitter and IR video stream of a F200 Intel RealSense camera running at 100 frames per second rate. A snapshot of the scene taken from the F200 IR video stream is shown below the mSAD data plot in FIG. 12. A person is sitting on a chair at about 3 feet distance from the F200 camera. mSAD data in FIG. 12 captured four full respiration cycles of the person.

Computing element (a desktop PC) was executing the same video frames processing algorithm described above to generate mSAD data both for F200 and for R200 cameras (FIGS. 11 and 12, respectively) in real time.

In the case of the dynamically projected patterns, as demonstrated on the example of a F200 Intel RealSence device (FIG. 12), body movements, including the ones associated with heartbeats and respiration, lead to the changes in the non-uniform illumination distribution of the scene created by the light emitter of the F200 device, as captured by the infrared camera of the F200 device (the captured non-uniform illumination distribution forms the artificial light texture), which otherwise would have been absent provided the absence of any motion in the scene.

One can note that there is a higher level of noise in the mSAD data in FIG. 12 compared to the mSAD data in FIG. 11. Said higher noise level can be explained by lack of synchronization between the patterns generation by the light emitter of the F200 camera and heartbeats and respiration of the person meaning that consecutive heartbeats and/or respiration cycles correspond to different average exposure of the body areas to the camera's patterns and also that different (but equal in duration) parts of a heartbeat time interval and/or of a respiration cycle duration correspond to different exposure of the body areas to the camera's patterns.

Note that, similarly to the first embodiment of a system according to the present invention, the distance between the F200 or R200 camera and the person can affect how pronounced the heartbeat signal will be during the respiration events. Generally, the closer the camera gets to the person the less pronounced the heartbeat signal component in the ALT data becomes during respiration events. Note also that at a large enough distance between the camera and the person there will be virtually no discernable pulse or respiration signal in the ALT data. Adjustments of the camera's position can be made, for example, based on observing visualizations of the collected ALT data.

Figure 13A:
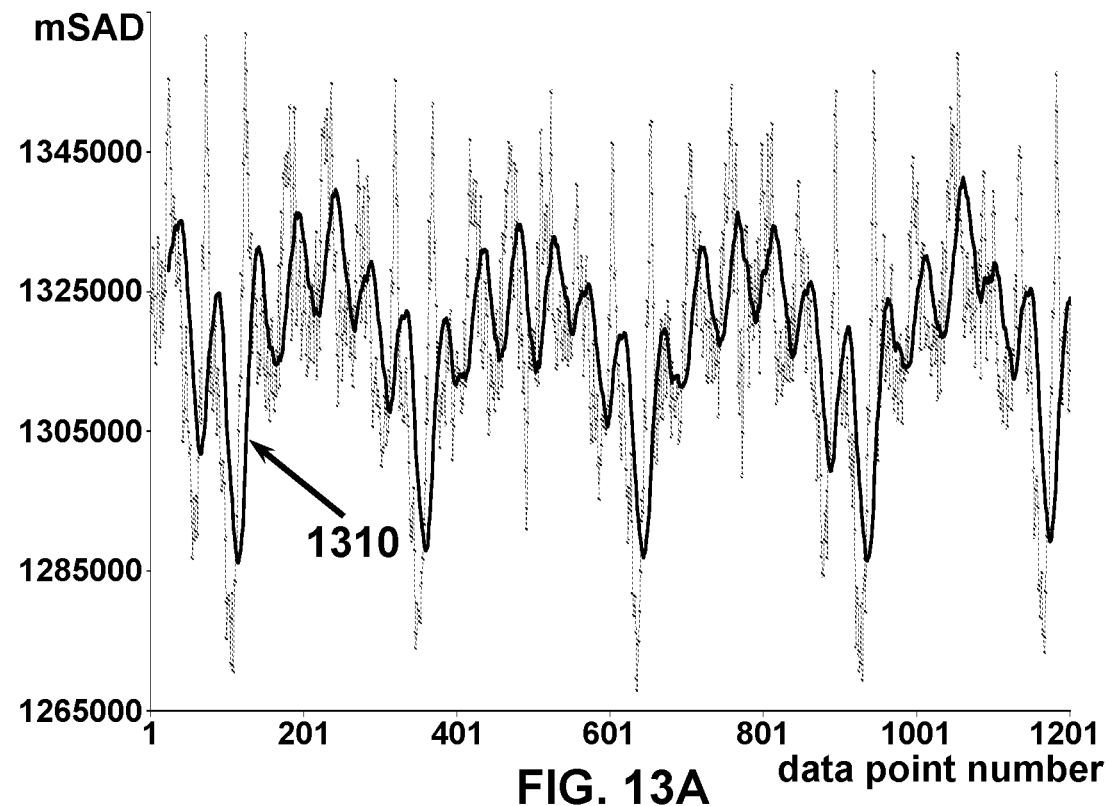
FIGS. 13A-B show dependence of the data, obtained by a system according to the present invention using a method according to the present invention, on the distance of said system from a person.
Figure 13B:
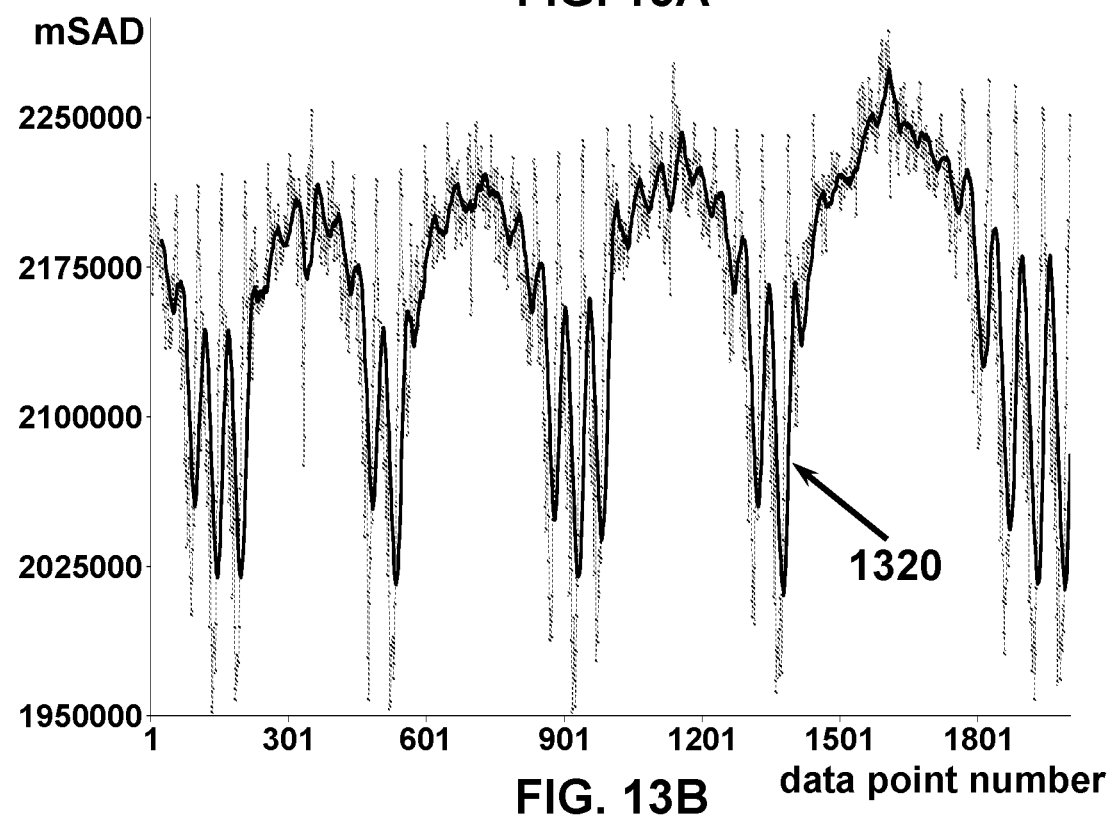

FIGS. 13A and 13B show mSAD data obtained using the IR light emitter and IR video stream of a R200 Intel RealSense camera running at 60 frames per second rate for two distances of the R200 camera from a person sitting in an armchair in front of the R200 camera, as shown in FIG. 11. FIG. 13A corresponds to the distance of ~152 cm (60 in) between the camera and the backrest of the armchair. FIG. 13B corresponds to the distance of ~102 cm (40 in) between the camera and the backrest of the armchair. mSAD data in both FIG. 13A and FIG. 13B captured four full respiration cycles of the person. Raw mSAD data are shown in FIGS. 13A and 13B by gray lines connecting the mSAD data points. Black lines 1310 and 1320 in FIG. 13A and FIG. 13B, respectively, are 24-points moving averages of the raw mSAD data. As data in FIGS. 13A and 13B demonstrate, variations in the mSAD data related to heartbeats are less pronounced during respiration cycles in FIG. 13B compared to FIG. 13A. One can also say that relative contribution of the respiration into the mSAD data increases with decreasing the distance between the person and the video camera and the light source elements (both elements are housed within the common enclosure of the R200 unit in this case).

Figure 14A:
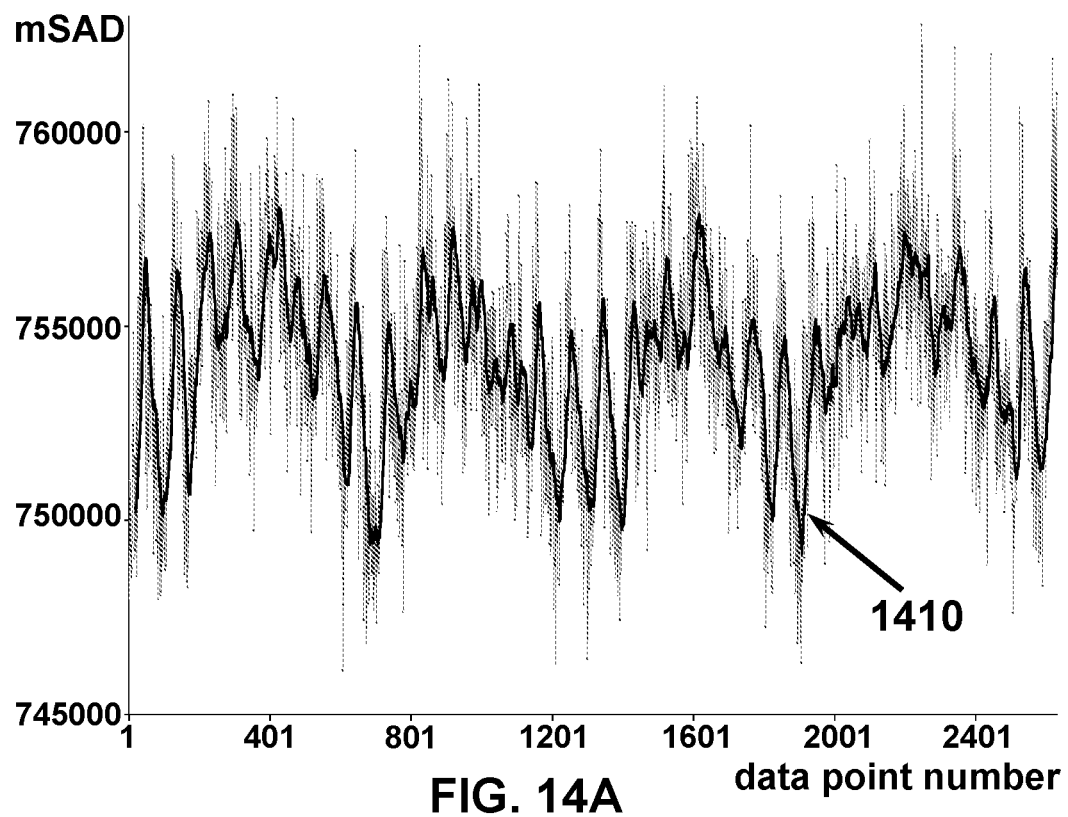
FIGS. 14A-B show dependence of the data, obtained by a system according to the present invention using a method according to the present invention, on the distance of said system from a person.
Figure 14B:
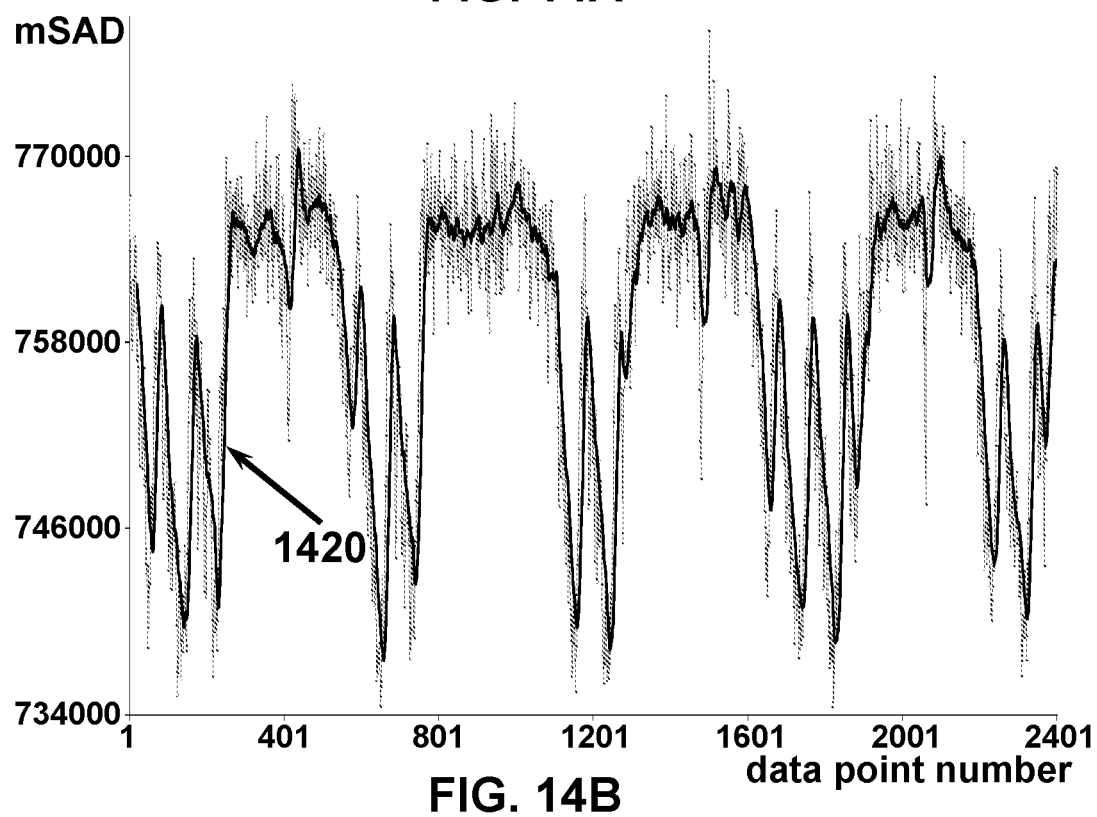

FIGS. 14A and 14B show mSAD data obtained using the IR light emitter and IR video stream of a F200 Intel RealSense camera running at 100 frames per second rate for two distances of the F200 camera from a person sitting on a chair in front of the F200 camera, as shown in FIG. 12. FIG. 14A corresponds to the distance of ~119 cm (47 in) between the camera and the backrest of the chair. FIG. 14B corresponds to the distance of ~81 cm (32 in) between the camera and the backrest of the chair. mSAD data in both FIG. 14A and FIG. 14B captured four full respiration cycles of the person. Raw mSAD data are shown in FIGS. 14A and 14B by gray lines connecting the mSAD data points. Black lines 1410 and 1420 in FIG. 14A and FIG. 14B, respectively, are 20-points moving averages of the raw mSAD data. As data in FIGS. 14A and 14B demonstrate, variations in the mSAD data related to heartbeats are less pronounced during respiration cycles in FIG. 14B compared to FIG. 14A. One can also say that relative contribution of the respiration into the mSAD data increases with decreasing the distance between the person and the video camera and the light source elements (both elements are housed within the common enclosure of the F200 unit in this case).

As different embodiments of the present invention described above demonstrate, systems and methods according to the present invention do not rely on any particular kind of light pattern (statically and/or dynamically projected). As comparison of the data shown in FIGS. 1 and 5A, 13A and 13B, and 14A and 14B demonstrates, the systems and methods of the present invention generate data exhibiting the same qualitative dependence on the distance between a person and the video camera and the light source elements. This dependence is related to the changes in responses of the elements of the additional light texture to the movements of the person's body, including the ones related to the person's heartbeats and respiration, as captured by a video camera element, with changing the distance between the person and the light source and the video camera elements, as shown above for one of the possible embodiments of a system according to the present invention (see FIGS. 9 and 10, and the related discussion above).

As demonstrated above, embodiments of the systems according to the present invention use inexpensive hardware components such as a Raspberry Pi single-board computer and a Pi NoIR camera, and are compatible with light emitters of different consumer electronics devices traditionally used for depth sensing applications, such as Kinect for Xbox 360, Intel RealSense R200 and F200 cameras, which generate vastly different, both in terms of the spatial characteristics and in terms of the temporal characteristics, light patterns.

As demonstrated above, methods according to the present invention use computationally simple algorithms based on the differential (between video frames) data processing and use of the integral values (a sum of the values calculated for pixels of a video frame) as a measure of motion in a video frame. Note that the methods of the present invention can be applied to the video frames not subjected to processing by a video encoder, as well as to the video frames processed by a video encoder. The methods according to the present invention enable one to use cheap video camera and computing elements and provide vast degree of compatibility with and independence of particular spatial and temporal characteristics of the light patterns generated by a light source element.

As demonstrated above, systems and methods according to the present invention do not use depth information encoded in the light patterns projected by the light emitters of the depth sensing devices such as Kinect and RealSense cameras used in some of the embodiments of the systems according to the present invention. As demonstrated above, systems and methods according to the present invention do not use or obtain distance information for any element of a scene, including a person's body or any part of said body. As also demonstrated above, systems and methods according to the present invention do not use or obtain information about position of any element of an image of a scene captured in a video frame by a video camera element within said image.

The preferred embodiment of a system according to the present invention includes a light source element which illuminates a set of areas of a person's body by creating light spots on those areas. Further, said light source element has at least one capability from the list comprising a capability to change the distance at least between two of said light spots, a capability to change the size of at least one of said light spots, a capability to change the shape of at least one of said light spots. Further, said light source element has a capability to change illumination intensity of said light spots. The preferred embodiment of a system according to the present invention includes a video camera element which has at least one capability from the list comprising a capability to change the rate of acquisition of video frames, and a capability to change the size of the video frames. The preferred embodiment of a system according to the present invention includes a computing element capable of performing computations of the sSAD and/or mSAD and/or XYabs numeric values (see above) for the video frames captured by the video camera element using a graphics processing unit (GPU).

The systems and methods of the present invention, as disclosed above, can be considered in relation to the other systems and methods suitable for obtaining said physiologic parameters of a person. Such consideration is presented below.

Methods, devices, and systems which can be used for determining respiration rate of a person, as disclosed in the U.S. Pat. Nos. 9,301,710, 9,226,691, 9,204,825, 9,204,824, 8,971,985, 8,792,969, which are incorporated herein by reference, rely on using and/or obtaining information about three-dimensional characteristics of at least a part of the person's body such as, for example, 3D profile of at least a part of the person's chest. Correspondingly, the main function of the light sources employed in the above-referenced inventions is to facilitate obtaining three-dimensional information relevant to at least a part of a person's body. Although such 3D information might be used for respiratory volume evaluation, information related to respiration and/or heart activity of a person (e.g. respiration rate and/or heart rate) can be determined without obtaining or using any 3D information for the whole or a part of a person's body or for any other element of a scene, as disclosed in the present invention.

Methods and devices which can be used for determining respiration rate of a person, as disclosed in the U.S. Pat. No. 6,352,517 are based on determining the distance between an illuminated area of a person's body and a source of light used for said illumination based on position of the light pattern reflected from the illuminated area on a position-sensitive detector. Similarly, methods and devices suitable for obtaining information related to respiration and/or heart activity of a person (e.g. respiration rate and/or heart rate) described in the U.S. Pat. No. 5,249,163 are based on detecting position of a light beam reflected by a surface on a position-sensitive detector. Similarly, methods and systems for non-invasively monitoring biological or biochemical parameters of an individual described in the U.S. Pat. No. 9,636,041 rely on obtaining a spatial correlation function between successive images in a sequence of images of a speckle pattern and further determining at least spatial position of a peak of the correlation function. As disclosed in the present invention, information related to respiration and/or heart activity of a person (e.g. respiration rate, heart rate, heart rate variability, respiration rate variability) can be obtained without obtaining or using position and/or distance information for any element of an image detected by a sensor of the video camera element of the present invention as well as without obtaining or using position and/or distance information for any feature of a function computed using one or more images detected by a sensor of the video camera element of the present invention.

Methods, devices, and systems for video-based determination of information related to respiration and/or heart activity of a person (e.g. respiration rate, heart rate) that do not rely on obtaining or using 3D information for at least a part of a person's body, such as the ones disclosed in the U.S. Pat. Nos. 9,364,157, 9,324,144, 9,305,350, 9,265,456, 9,262,826, 8,897,522, 8,855,384, 8,693,735, 7,477,571 and the patent application Ser. No. 13/850,717, which are incorporated herein by reference, and as disclosed in the work (Chen J., Chang Z., Qiu Q., Li X., Sapiro G., Bronstein A., Pietikäinen M. "RealSense=Real Heart Rate: Illumination Invariant Heart Rate Estimation from Videos", 6th International Conference on Image Processing Theory Tools and Applications (IPTA), 12-15 Dec. 2016, Oulu, Finland, doi: 10.1109/IPTA.2016.7820970), which is incorporated herein by reference, derive numeric values representative of the vital signs of a person by processing time series of numeric values other than the types of values (e.g. sSAD or mSAD or XYabs) obtained according to the present invention.

Further, methods, devices, and systems, as disclosed in the U.S. Pat. Nos. 9,364,157, 9,324,144, 9,305,350, 9,265, 456, 9,262,826, 8,897,522, 8,855,384, 8,693,735, 7,477,571 and the patent application Ser. No. 13/850,717 lack use of a dedicated light source element and/or lack use of its function of illuminating a set of areas of a person's body according to the present invention, which prevents the inventions disclosed in the U.S. Pat. Nos. 9,364,157, 9,324,144, 9,305, 350, 9,265,456, 9,262,826, 8,897,522, 8,855,384, 8,693,735, 7,477,571 and the patent application Ser. No. 13/850,717 to exploit the main effect of the light source element and of its function according to the present invention, as disclosed above.

Although the authors of said work by Chen et al. used an Intel RealSense camera which can be used by the systems according to the present invention, the purpose of using said camera in the work by Chen et al. was to obtain 3D data for a scene observed by the camera in order to facilitate region of interest location (location of the cheek region of a person's face). More importantly, the average pixel intensity for the pixels in the region of interest in each of the infrared video frames collected by the camera formed the set of numeric values which was used in said work by Chen et al. to obtain numeric values representative of the heart rate of the person, instead of using differential measures of variation between the video frames according to the present invention. The use of an average pixel intensity value for the pixels in the region of interest effectively prevents utilization of the main effect of the light source element and of its function according to the present invention, as disclosed above, by "blending" the elements of the artificial light texture, which could be created by the light source element, via the averaging procedure used to obtain said average pixel intensity value for a collected video frame. Contrary to the methods of the present invention, average illumination-based approaches to the video frames processing can not capture displacements or changes in the shape or changes in the size or changes in the numbers of the elements of the additional light texture if said displacements and/or changes are not accompanied by changes in the overall illumination captured in the video frames. Moreover, average illumination-based approaches can capture the changes in the illumination of the elements of the additional light texture only to the extent such changes contribute to the change in the overall illumination in the video frames. Said utilization of the main effect of the light source element and of its function for the purpose of the present invention is best achieved via use of the differential measures of variation between the video frames according to the present invention, as disclosed and as demonstrated on a number of examples above.

Further, methods, devices, and systems, as disclosed in the U.S. Pat. Nos. 9,364,157, 9,324,144, 9,305,350, 9,265, 456, 9,262,826, 8,897,522, 8,855,384, and as disclosed in said work by Chen et al. contain requirements to have an area of skin exposed to the systems and devices disclosed therein. The invention disclosed in this patent application removes such requirement of having an area of open skin due to the fact that methods and systems according to the present invention will function in situations when a person is completely covered by one or more covering items as long as the motions of the person's body which are related to the person's respiration and/or heartbeats are at least partially imparted onto said one or more covering items, as discussed and as demonstrated on a number of examples above.

Methods, devices, and systems for video-based respiration rate determination that use optical flow based estimations for object motion in a series of video frames are described in the works (Nakajima K., Osa A., Miike H. "A method for measuring respiration and physical activity in bed by optical flow analysis" in Proceedings of the 19th Annual International Conference of the IEEE Engineering in Medicine and Biology Society, 1997, vol. 5, pp. 2054-2057, doi: 10.1109/IEMBS.1997.758752), (Nakajima K., Matsumoto Y., Tamura T. "Development of real-time image sequence analysis for evaluating posture change and respiratory rate of a subject in bed", Physiological Measurement, 2001, vol. 22, no. 3, N21-8, doi: 10.1088/0967-3334/22/3/401), and (Kuo Y.-M., Lee J.-S., Chung P. "A Visual Context-Awareness-Based Sleeping-Respiration Measurement System", IEEE Transactions on Information Technology in Biomedicine, 2010, vol. 14, no. 2, pp. 255-265, doi: 10.1109/TITB.2009.2036168) which are incorporated herein by reference. Importantly, these works consider elements of a person's body or elements of a blanket covering the person to be the objects in a series of video frames. Optical flow-based methods require that illumination of the pixels associated with an object remains constant between the consecutive video frames. Because of this requirement, such methods benefit from use of light sources that provide uniform illumination of a scene. Contrary to that, the function of a light source element according to the present invention is to illuminate a set of areas of a person's body. The main effect of the light source element and its function according to the present invention is to impart additional (artificial) light texture to at least a part of the person's body. With the added light texture preferably characterized by having a number of distinct illumination areas, utilization of a light source element and its function according to the invention disclosed in this patent application creates conditions which are incompatible with utilization of the optical flow-based video processing methods for respiration rate and/or heart rate determination in which the objects in a series of video frames are elements of a person's body or elements of a blanket covering the person.

We should note that elements of the artificial light texture produced by operation of a light source element according to the present invention can be considered to be the potential objects in a series of video frames of a scene for the purposes of the optical flow-based analysis, as opposed to considering elements of a person's body or a blanket as the objects in a series of video frames of a scene in the works referred to above, so that optical flow-based methods of video analysis can be applied to these artificial light texture elements created by operation of a light source element according to the present invention.

As demonstrated above, there is substantial patent and non-patent literature devoted to the devices and methods for non-contact measurement of physiologic parameters of a person, including heart rate and respiration rate, which indicates existence of a substantial interest and need in such devices and methods. Also, Intel, the manufacturer of RealSense cameras, provides pulse detection capability in their RealSense software development kit (SDK) which requires tracking the face of a person and is based on methods other than the ones according to the present invention (see, for example, reference 8 in the list of references below). Despite the existence of said interest and need, computationally simple methods of the present invention which can be used with a vast variety of light sources and light patterns generated by those light sources, do not involve obtaining or using any distance or position information, and do not require any areas of open skin for them to work were not suggested before, which attests to the non-obviousness of the systems and methods according to the present invention.

REFERENCES

Each of the referenced documents in the references 1-8 below is incorporated herein by reference, and the copies of the referenced documents accompany the present application.

1. "H.264/MPEG-4 AVC", retrieved on Jul. 14, 2017 from the Internet: <URL: https://en.wikipedia.org/wiki/H.264/MPEG-4_AVC>.
2. "Sum of absolute differences", retrieved on Jul. 14, 2017 from the Internet: <URL: https://en.wikipedia.org/wiki/Sum_of_absolute_differences>.
3. "Short-time Fourier transform", retrieved on Jul. 14, 2017 from the Internet: <URL: https://en.wikipedia.org/wiki/Short-time_Fourier_transform>.
4. Keselman L., Woodfill J. I., Grunnet-Jepsen A., Bhowmik A. "Intel® RealSense™ Stereoscopic Depth Cameras", retrieved on Jun. 20, 2017 from the Internet: <URL: https://arxiv.org/pdf/1705.05548.pdf> (arXiv: 1705.05548v1); the paper was posted to arxiv.org on May 16, 2017.
5. "Utility for changing laser camera parameters (IVCAM v0.5)", retrieved on Jul. 14, 2017 from the Internet: <URL: https://software.intel.com/en-us/forums/realsense/topic/537872>, individual posts show their respective dates.
6. "Taxicab geometry", retrieved on Jul. 14, 2017 from the Internet: <URL: https://en.wikipedia.org/wiki/Taxicab_geometry>.
7. "Macroblock", retrieved on Jul. 14, 2017 from the Internet: <URL: https://en.wikipedia.org/wiki/Macroblock>.
8. "Pulse Detection with Intel® RealSense™ Technology", retrieved on Jul. 14, 2017 from the Internet: <URL: https://software.intel.com/en-us/articles/pulse-detection-with-intel-realsense-technology>.

LISTING 1

```
#!python3
#Please see picamera.readthedocs.io for the 'picamera' library documentation.
import picamera
import numpy as np
import picamera.array
import time
import datetime
import os
experimentDurationHours = 0.5 #Duration of the ALT data collection, hours.
timeSliceDurationMinutes = 6  #The whole 'experimentDurationHours' time is split into
                              # 'timeSliceDurationMinutes' minutes long intervals ('time
                              # slices').
experimentDir = "./experiment/"   #Location where ALT data, video, etc. will be saved.
                                  # Each 'time slice' has its own sub-folder, see below.
os.makedirs(experimentDir)
class ALT(picamera.array.PiMotionAnalysis):
    def analyse(self, a):
        #This is the "sSAD" value referred to above:
        sSAD = np.sum(a['sad'])
        sSADs.append(sSAD)
        #Note that the sSAD value for an I-frame in the captured video data stream will be
        # equal to zero. Please consult documentation for the 'start_recording( )' method of
        # the 'picamera.PiCamera' class
        # (picamera.readthedocs.io/en/release-1.12/api_camera.html#picamera.PiCamera.start_recording).
        # Particularly, setting the 'intra_period' parameter of the 'start_recording( )' method
        # to zero will cause "the encoder to produce a single initial I-frame, and then only
        # P-frames subsequently". If you would like to keep I-frames in the captured video
        # stream, you can adjust the 'intra_period' parameter accordingly (or leave it at its
        # default value). A way to process the I-frame sSAD values would be to replace
        # them with the sSAD value of the previous frame, as the following 'pseudo code'
        # shows:
```

LISTING 1

```
    #if sSAD != 0:
        #sSADsNoZeros.append(sSAD)
    #else:
        #if len(sSADsNoZeros) >= 1:
            #sSADsNoZeros.append(sSADsNoZeros[-1])
with picamera.PiCamera( ) as camera:
    with ALT(camera) as mvdOutput: # motion vector data (mvd) output
        camera.resolution = (1280, 720)
        camera.framerate = 49
        camera.exposure_mode = 'night'
        camera.awb_mode = 'auto'
        camera. iso = 1600
        camera.sharpness = 100
        camera.contrast = 100
        while camera.analog_gain <= 1:
            time.sleep(0.1)
        #'seep' delays below give you some time before the camera parameters are locked
        # and video recording and ALT data collection start
        # which might be helpful, for example, if you start ALT before going to sleep
        # so that there is time for you to turn off the lights and let the camera adjust to
        # low-light environment.
        print('Preparing ...')
        print('60 ...')
        time.sleep(45)
        print('15 ...')
        time.sleep(5)
        #Fixing the camera's video acquisition parameters:
        camera.shutter_speed = camera.exposure_speed
        camera.exposure_mode = 'off'
        g = camera.awb_gains
        camera.awb_mode = 'off'
        camera.awb_gains = g
        print('10 ...')
        time.sleep(5)
        print('5 ...')
        time.sleep(5)
        print('RUNNING ...')
        for t in range(int(experimentDurationHours*60/timeSliceDurationMinutes)):
            startDateTime = datetime.datetime.now( )
            timeSliceDir = experimentDir + str(startDateTime) + '/'
            print('timeSliceDir = ', timeSliceDir)
            os.makedirs(timeSliceDir)
            sSADs = [ ]
            sSADsfile = open(timeSliceDir + 'SADs.txt', 'w')
            #Note that the 'quality' parameter of the 'start_recording( )' method might be
            # useful to keep the size of the captured video files reasonably low.
            # Please see
            # picamera.readthedocs.io/en/release-1.12/api_camera.html#picamera.PiCamera.start_recording
            # for details.
            camera.start_recording(timeSliceDir + '1280×720.h264', format = 'h264',
            motion_output = mvdOutput)
            camera.wait_recording(timeSliceDurationMinutes*60)
            camera.stop_recording( )
            #Note that saving ALT data into a file and stopping/restarting video recording will
            # cause a short time 'gap' between the consecutive "time slices"
            for i in range(len(sSADs)):
                sSADsfile.write(str(i + 1) + ": " + str(sSADs[i]) + "\n")
        sSADsfile.close( )
```

The invention claimed is:

1. A method of obtaining information related to at least one of: a respiration rate of a person, a heart rate of the person, a respiration rate variability of the person, a heart rate variability of the person, a temporal characteristic of at least a part of a heartbeat of the person, or a temporal characteristic of at least a part of a respiration cycle of the person, comprising the steps of:
   1) illuminating a set of areas of the person's body using a light source;
   2) collecting a video frames set for at least one of the illuminated areas using a video camera;
   3) performing computations for at least two video frames of the video frames set to result in a set of numeric values for the video frames set using a computer; and
   4) performing computations for at least a part of the set of numeric values using the computer to obtain numeric values related to the at least one of: the respiration rate of the person, the heart rate of the person, the respiration rate variability of the person, the heart rate variability of the person, the temporal characteristic of at least a part of a heartbeat of the person, or the temporal characteristic of at least a part of a respiration cycle of the person, or display said at least a part of the set of numeric values using a graphical representation of said at least a part of the set of numeric values, wherein step 1) results in the set of areas of the person's body receiving more photons during the exposure time period for any frame of the video frames set than the set of areas of the person's body would have received during the exposure time period for any frame of the video frames set without performing step 1) and under the otherwise identical conditions, wherein said video frames set has at least three video frames, wherein each video frame in said video frames set has at least two pixels, wherein the step 3) comprises the steps of:
  i) for each video frame in the at least two video frames of the video frames set performing computations comprising the steps of:
    a) for each pixel of at least a part of the video frame associating a numeric value with the pixel using video frame data of the video frame;
    b) for each pixel of at least a part of another video frame in said video frames set associating a numeric value with the pixel using video frame data of the another video frame;
    c) for each pixel of said at least a part of the video frame calculating a difference between the numeric value associated with the pixel and the numeric value associated with a pixel of said at least a part of another video frame;
    d) for each pixel of said at least a part of the video frame calculating a numeric value equal to at least one of: an absolute value of the difference or a squared value of the difference; and
    e) calculating a sum of the numeric values calculated for the pixels of said at least a part of the video frame in the step d) to result in a numeric value for the video frame, and wherein the method does not use or obtain any information about any distance related to any element of a scene captured in any video frame of said video frames set and the method does not use or obtain any information about position of any element of an image of a scene captured in any video frame of said video frames set within said image.

2. The method of claim 1, wherein a ratio of average illumination for two areas of the person's body captured in a frame of said video frames set is at least $1+1/(2^n-2)$, wherein n is a number of bits in a binary representation of a numeric value associated with a pixel of said frame and contained in video frame data of said frame, and said ratio is determined using the numeric values associated with pixels of said frame and contained in the video frame data of said frame, wherein the pixels correspond to said two areas of the person's body.

3. The method of claim 2, wherein n equals 16 and the ratio of the average illumination for two areas of the person's body captured in a frame of said video frames set is at least 1.01.

4. The method of claim 2, wherein n equals 16 and the ratio of the average illumination for two areas of the person's body captured in a frame of said video frames set is at least 1.1.

5. The method of claim 1, wherein the numeric values associated with said each pixel of at least a part of the video frame of and the numeric values associated with said each pixel of at least a part of another video frame in the step i) of step 3) are obtained using a same set of rules.

6. The method of claim 1, wherein a pixel row number for said pixel of the video frame and a pixel row number for said pixel of said another video frame in the step c) of step i) of step 3) are equal, as well as a pixel column number for said pixel of the video frame and a pixel column number for said pixel of said another video frame in the step c) of step i) of step 3) are equal.

7. The method of claim 1, wherein said pixel of said another video frame in the step c) of step i) of step 3) is selected by a video encoder.

8. The method of claim 1, wherein the step 3) comprises replacing at least one numeric value in said set of numeric values for said video frames set by another numeric value from said set of numeric values for said video frames set.

9. The method of claim 1, wherein said graphical representation of said at least a part of the set of numeric values is a two-dimensional plot.

10. The method of claim 1, comprising saving at least one video frame of the video frames set to a local or remote storage medium.

11. The method of claim 1, comprising saving at least one numeric value of said set of numeric values for the video frames set to a local or remote storage medium.

12. The method of claim 1, comprising of saving at least one numeric value of said numeric values related to the at least one of:
  the respiration rate of the person, the heart rate of the person, the respiration rate variability of the person, the heart rate variability of the person, the temporal characteristic of at least a part of a heartbeat of the person, or the temporal characteristic of at least a part of a respiration cycle of the person to a local or remote storage medium.

13. The method of claim 2, wherein the numeric values associated with said each pixel of at least a part of the video frame and the numeric values associated with said each pixel of at least a part of another video frame in the step i) of step 3) are obtained using a same set of rules.

14. A system for obtaining information related to at least one of: a respiration rate of a person, a heart rate of the person, a respiration rate variability of the person, a heart rate variability of the person, a temporal characteristic of at least a part of a heartbeat of the person, or a temporal characteristic of at least a part of a respiration cycle of the person, comprising:
  1) a light source element configured to illuminate a set of areas of the person's body;
  2) a video camera element configured to collect a video frames set for at least one of the illuminated areas; and
  3) a computing element and a non-transitory storage medium readable by the computing element and storing instructions that, when executed by the computing element, cause the computing element to perform computations comprising the steps of:
    i) performing computations for at least two video frames of the video frames set to result in a set of numeric values for the video frames set; and
    ii) performing computations for at least a part of the set of numeric values to result in at least one of:
      obtaining numeric values related to the at least one of: the respiration rate of the person, the heart rate of the person, the respiration rate variability of the person, the heart rate variability of the person, the temporal characteristic of at least a part of a heartbeat of the person, or the temporal characteristic of at least a part of a respiration cycle of the person, or
      displaying at least a part of the set of numeric values using a graphical representation of said at least a part of the set of numeric values, wherein the step i) comprises:
performing computations for each video frame in the at least two or more video frames of the video frames set, performing computations comprising the steps of:
a) for each pixel of at least a part of the video frame associating a numeric value with the pixel using video frame data of the video frame;
b) for each pixel of at least a part of another video frame in said video frames set associating a numeric value with the pixel using video frame data of the another video frame;
c) for each pixel of said at least a part of the video frame calculating a difference between the numeric value associated with the pixel and the numeric value associated with a pixel of said at least a part of another video frame;
d) for each pixel of said at least a part of the video frame calculating a numeric value equal to at least one of: an absolute value of the difference or a squared value of the difference; and
e) calculating a sum of the numeric values calculated for the pixels of said at least a part of the video frame in the step d) to result in a numeric value for the video frame;
wherein any of said computations performed by the computing element do not use or obtain any information about any distance related to any element of a scene captured in any video frame of said video frames set, and any of said computations performed by the computing element do not use or obtain any information about position of any element of an image of a scene captured in any video frame of said video frames set within said image.

15. The system of claim 14, wherein the type of said computing element is one of: a computer, a single-board computer, a tablet, or a smartphone.

16. The system of claim 14, wherein said computing element has a graphics processing unit.

17. The system of claim 14, wherein said light source element is a light source having a distribution of wavelengths with a maximum above 750 nm.

18. The system of claim 14, wherein said light source element is a light source having a distribution of wavelengths with a maximum in the range from 350 to 750 nm.

19. The system of claim 14, wherein said light source element is a laser.

20. The system of claim 14, wherein said light source element is configured to illuminate said areas by producing light spots on said areas, wherein the light spots have illumination maxima separated by at least 1 nm distance for at least two of said light spots.

21. The system of claim 14, wherein said light source element is configured to illuminate said areas by producing light spots on said areas, wherein the light spots have illumination maxima separated by at least 1000 nm distance for at least two of said light spots.

22. The system of claim 14, wherein said light source element is configured to illuminate said areas by producing a set of light spots on said areas, wherein the light spots have illumination maxima separated by at least 1 mm distance for at least two of said light spots.

23. The system of claim 16, wherein at least a part of any of said computations is performed using said graphics processing unit.

24. The system of claim 14, wherein said light source element is configured to illuminate said areas by creating light spots on said areas, wherein the light spots are separated from each other by areas of the person's body having lower illumination compared to that of the light spots.

25. The system of claim 14, wherein said light source element is configured to illuminate said areas by creating light spots on said areas, and wherein said light source element has a capability to change at least one of: a distance at least between two of said light spots, a size of at least one of said light spots, a shape of at least one of said light spots, or illumination intensity of at least one of said light spots.

26. The system of claim 14, wherein a ratio of average illumination for two areas of the person's body captured in a video frame of the video frames set is at least $1+1/(2^n-2)$, wherein n is a number of bits in a binary representation of a numeric value associated with a pixel of the video frame and contained in video frame data of the video frame, and the ratio is determined using the numeric values associated with pixels of the video frame and contained in the video frame data of the video frame, wherein the pixels correspond to the two areas of the person's body.

27. The method of claim 1, wherein said illuminating a set of areas comprises creating light spots on said areas, wherein the light spots are separated from each other by areas of the person's body having lower illumination compared to that of the light spots.

* * * * *